US006123949A

United States Patent [19]

Cochran et al.

[11] Patent Number: 6,123,949

[45] Date of Patent: Sep. 26, 2000

[54] RECOMBINANT FOWLPOX VIRUS S-FPV-043 AND USES THEREOF

[76] Inventors: Mark D. Cochran, 4506 Horizon Dr., Carlsbad, Calif. 92008; David E. Junker, 6901 Galewood St., San Diego, Calif. 92120

[21] Appl. No.: 08/479,869

[22] Filed: Jun. 7, 1995

Related U.S. Application Data

[63] Continuation of application No. 08/024,156, Feb. 26, 1993.

[51] Int. Cl.[7] ...................... A61K 39/275; A61K 39/285; A61K 39/12

[52] U.S. Cl. .................................... 424/232.1; 424/199.1; 424/93.2; 435/235.1; 435/320.1; 435/69.1; 435/69.3; 435/172.3; 935/65

[58] Field of Search ............................. 435/235.1, 320.1, 435/69.1, 69.3, 172.3; 424/199.1, 93.2, 432.1; 935/65

[56] References Cited

U.S. PATENT DOCUMENTS

| | | | |
|---|---|---|---|
| 5,093,258 | 3/1992 | Cohen et al. . | |
| 5,174,993 | 12/1992 | Paoletti . | |
| 5,180,675 | 1/1993 | Drillen et al. | 435/235.1 |
| 5,182,210 | 1/1993 | Binns et al. . | |
| 5,204,243 | 4/1993 | Paoletti . | |
| 5,258,294 | 11/1993 | Boyle et al. . | |
| 5,286,639 | 2/1994 | Yanagida et al. | 435/235.1 |
| 5,310,671 | 5/1994 | Binns et al. . | |
| 5,332,676 | 7/1994 | Binns et al. . | |
| 5,368,855 | 11/1994 | Boyle et al. . | |
| 5,369,025 | 11/1994 | Nazerian et al. . | |
| 5,374,558 | 12/1994 | Binns et al. . | |
| 5,387,519 | 2/1995 | Yanagida et al. . | |
| 5,403,582 | 4/1995 | Nazerian et al. . | |
| 5,443,831 | 8/1995 | Keeler et al. . | |
| 5,505,941 | 4/1996 | Paoletti . | |
| 5,514,375 | 5/1996 | Paoletti et al. . | |

FOREIGN PATENT DOCUMENTS

| | | |
|---|---|---|
| 0284416 | 9/1988 | European Pat. Off. . |
| 404576A3 | 12/1990 | European Pat. Off. . |
| 517292A1 | 12/1992 | European Pat. Off. . |
| 520753A1 | 12/1992 | European Pat. Off. . |
| 314569B1 | 3/1994 | European Pat. Off. . |
| 308220B1 | 6/1994 | European Pat. Off. . |
| 284416B1 | 2/1995 | European Pat. Off. . |
| 338807B1 | 11/1995 | European Pat. Off. . |
| WO8802022 | 3/1988 | WIPO . |
| WO8903429 | 4/1989 | WIPO . |
| WO8903879 | 5/1989 | WIPO . |
| WO8907644 | 8/1989 | WIPO . |
| WO8912684 | 12/1989 | WIPO . |
| WO9004638 | 5/1990 | WIPO . |
| WO9012882 | 11/1990 | WIPO . |
| WO9112318 | 8/1991 | WIPO . |
| WO9102072 | 3/1992 | WIPO . |
| WO9203545 | 3/1992 | WIPO . |
| WO9222641 | 12/1992 | WIPO . |
| WO9303145 | 2/1993 | WIPO . |

OTHER PUBLICATIONS

Boursnell, Micahel E.G. et al. (1992) "Avipoxvirus Vectors", Recomb. Poxviruses (1992), 269–83. Editors(s): Binns, Matthew, M.; Smith, Geoffrey L. Publisher: CRC, Boca Raton, Fla. Coden (Exhibit B).

MccMillen, J.K. et al. (1993) "The Safe And Effective Use of Fowlpox Virus As A Vector For Poultry Vaccines", Brown, F. (Ed.) Developments in Biological Standardization, vol. 82. Recombinant Vectors In Vaccines Development; Symposium, Albany, NY, USA, May 23–26, 1993 VIII+268P.S. Karger AG: Basel, Switzerland; New York, New York, USA (Exhibit C).

Zantinge J.L. et al., "Analysis Of Fowlpox Virus DNA Replication And Mapping" Can. J. Microbiol., vol. 41, No. 4–5, 1995, pp. 378–387 (Exhibit D).

Mueller, H.K. et al. (1977) "Comparison of 5 Poxvirus Genomes By Analysis With Restriction Endonucleases Hin–D–III Bam–I and Eco–R–I", Virology 38:135–148 (Ex. 37).

Boyle, D.B. and Coupar B.E.H. (1986) "Identification and Cloning of the Fowlpox Virus Thymidine Kinase Gene Using Vaccinia Virus", Virology 67:1591–1600 (Ex. 38).

Boyle, D.B. et al. (1987) "Fowlpox Virus Thymidine Kinase Nucleotide Sequence and Relationships to Other Thymidine Kinases", Virology 156:355–365 (Ex. 39).

Schnitzlein, W.M. et al. (1988) "Genomic and Antigenic Characterization of Avipoxviruses", Virus Research 10:65–76 (Ex. 40).

Boyle, D.B. and Coupar, B.E.H. (1988) "Consturction of Recombinant Fowlpox Viruses as Vectors For Poultry Vaccines", Virus Research 10:343–356 (Ex. 41).

Tomley, F. et al. (1988) "Sequence Analysis of an 11.2 Kilobase Near–Terminal Bam–H–I Fragment of Fowlpox Virus", Journal of General Virology 69:1025–1040 (Ex. 42).

Binns, M.M. et al. (1988) "Comparison of A Conserved Region In Fowlpox Virus And Vaccinia Virus Genomes and the Translocation of the Fowlpox Virus Thymidine Kinase Gene", Journal of General Virology 69:1275–1284 (Ex. 43).

Taylor, J. And Paoletti, E. (1988) "Fowlpox Virus as a Vector in Non–Avian Species", Vaccine 6:466–468 (Ex. 44).

Campbell, J.I.A. et al. (1989) "Tandem Repeated Sequences With The Terminal Region of the Fowlpox Virus Genome", Journal of General Virology 70:145–154 (Ex. 45).

(List continued on next page.)

*Primary Examiner*—Lynette R. F. Smith
*Assistant Examiner*—Datquan Lee
*Attorney, Agent, or Firm*—John P. White; Cooper & Dunham LLP

[57] ABSTRACT

The present invention provides a recombinant fowlpox virus designated S-FPV-043 (ATCC Accession No. VR 2395). A vaccine useful for immunizing an animal against fowlpox virus and Newcastle disease virus is provided which comprises an effective immunizing amount of S-FPV-043 and a suitable carrier. A method of immunizing an animal against fowlpox virus and Newcastle disease virus is also provided which comprises administering to the animal an effective immunizing dose of the vaccine.

12 Claims, 3 Drawing Sheets

OTHER PUBLICATIONS

Taylor, J. et al. (1988) "Recombinant Fowlpox Virus Inducing Protective Immunity In Non–Avian Species", Vaccine 6:497–503 (Ex. 46).
Taylor, J. et al. (1988) "Protective Immunity Against Avian Influenza Induced By A Fowlpox Virus Recombinant", Vaccine 6:504–508 (Ex. 47).
Yanagida, N. et al. (1990) "Protective Immunity Against Newcastle Disease Virus Induced By Fowlpox Virus Recombinants", Vaccines 90, Cold Spring Harbor Laboratory Press 85–89 (Ex. 48).
Spehner, D. et al. (1990) "Construction of Fowlpox Virus Vectors With Intergenic Insertions Expression of the Beta Galactosidase Gene and the Measles Virus Fusion Gene", Journal of Virology 64:1441–1450 (Ex. 49).
Kumar S. and Boyle, D.B. (1990) "Mapping of a Major Early–Late Gene of Fowlpox Virus", Virus Research 15:175–186 (Ex. 50).
Taylor, J. et al. (1990) "Newcastle Disease Virus Fusion Protein Expressed in a Fowlpox Virus Recombinant Confers Protection in Chickens", Journal of Virology 64:1441–1450 (Ex. 51).
Boursnell, M.E.G. et al. (1990) "Insertion of the Fusion Gene from Newcastle Disease Virus Into A Non–Essential Region In The Terminal Repeats of Fowlpox Virus and Demonstration of Protective Immunity Induced by the Recombinant", Virology 71:621–628 (Ex. 52).
Dhawale, S.S. and Nazerian K. (1990) "Construction of Recombinant Fowlpox Virus Expressing Bacterial Betagalactosidase in Chick Embryo Fibroblasts", Abstr Annu Meet Am Soc Microbiol 90:333 (Ex. 53).
Tripathy, D.N. and Wittek, R. (1990) "Regulation of Foreign Gene in Fowlpox Virus By a Vaccinia Virus Promoter", Avain Diseases 34:218–220 (Ex. 54).
Prideaux, C.T. et al. (1990) "Comparative Analysis of Vaccinia Virus Promoter Activity in Fowlpox and Vaccinia Virus Recombinants", Virus Res 16:43–58 (Ex. 55).
Tartaglia, J. et al. (1990) "Nucleotide Sequence Analysis of a 10.5 Kbp Hin–D–III Fragment of Fowlpox Virus Relatedness to the Central Portion of the Vaccinia Virus Hin–D–III D Region", Virology 71:1517–1524 (Ex. 56).
Kumar, S. and Boyle D.B. (1990) "Activity of a Fowlpox Virus Late Gene Promoter in Vaccinia and Fowlpox Virus Recombinants", Archives of Virology 112:139–148 (Ex. 57).
Boursnell, M.E.G. et al. (1990) "A Recombinant Fowlpox Virus Expressing the Hemagglutinin–Neuraminidase Gene To Newcastle Diseaase Virus NDV Protects Chickens Against Challenge By NDV", Virology 178:297–300 (Ex. 58).
Kumar, S. and Boyle D.B. (1990) "A Poxvirus Bidirectional Promoter Element with Early–Late and Late Functions", Virology 179:151–158 (Ex. 59).
Coupar, B.E.H. et al. (1990) "Restriction Endonuclease Mapping of the Fowlpox Virus Genome", Virology 179:159–167 (Ex. 60).
Wild, F. et al. (1990) "Fowlpox Virus Recombinant Encoding the Measles Virus Fusion Protein Protection of Mice Against Fatal Measles Encephalitis", Vaccine 8:441–442 (Ex. 61).
Ogawa, R. et al. (1990) "Recombinant Fowlpox Viruses Inducing Protective Immunity Against Newcastle Disease and Fowlpox Virus", Vaccine 8:486–490 (Ex. 62).
Edbauer, C. et al. (1990) "Protection of Chickens With a Recombinant Fowlpox Virus Expressing the Newcastle Disease Virus Hemagglutinin–Neuraminidase Gene", Virology 179:901–904 (Ex. 63).
Binns, M.M. et al. (1990 "Analysis of the Fowlpox Virus Genome Region Correspinding to the Vaccinia Virus D6 to A1 Region Location of and Variation in Non–Essential Genes in Poxviruses", Journal of General Virology 71:2873–2882 (Ex. 64).
Nazerian, K. And Dhawale, S. (1991) "Structural Analysis of Unstable Intermediate and Stable Forms of Recombinant Fowlpox Virus", Virology 72:2792–2795 (Ex. 65).
Tripathy, D.N. and Schnitzlein, W.M. (1991) "Expression of Avian Influenza Virus Hemagglutinin By Recombinant Fowlpox Virus", Avain Diseases 35:186–191 (Ex. 66).
Taylor, J. et al. (1991) "Efficacy Studies on a Canarypox–Rabies Recombinant Virus", Vaccine 9:190–193 (Ex. 67).
Webster, R.G. et al. (1991) "Efficacy of Nucleoprotein and Hemagglutinin Antigens Expressed In Fowlpox Virus as Vaccine For Influenza in Chickens", Vaccine 9:303–308 (Ex. 68).
Beard, C.W. et al. (1991) "Protection of Chickens Against Highly Pathogenic Avian Influenza Virus H5N2 By Recombinant Fowlpox Viruses", Avian Disease 35:356–359 (Ex. 69).
Iritani, Y. et al. (1991) "Antibody Response To Newcastle Disease Virus NDV of Recombinant Fowlpox Virus Fpv Expressing a Hemagglutinin–Neuraminidase of Ndv into Chickens in the Presence of Antibody to NDV or FPV", Avain Diseases 35:659–661 (Ex. 70).
Bayliss, C.D. et al. (1991) "A Recombinant Fowlpox Virus That Expresses the Vp2 Antigen of Infectious Bursal Disease Virus Induces Protection Against Mortality Caused By the Virus", Archives of Virology 120:193–205 (Ex. 71).
Yanagida, N. et al. (1992) "Recombinant Fowlpox Viruses Expressing the Glycoprotein B Homolog and the Pp38 Gene Marek's Disease Virus", Journal of Virology 66:1402–1408 (Ex. 72).
Nazerian, K. et al. (1992) "Protection Against Marek's Disease By a Fowlpox Virus Recombinant Expressing the Glycoprotein B or Marek's Disease Virus", Journal of Virology 66:1409–1413 (Ex. 73).
Boyle D.B. (1992) "Quantitative Assessment of Poxvirus Promoters in Fowlpox and Vaccinia Virus Recombinants", Virus Genes 6:281–290 (Ex. 74).
Mockett, B. et al. (1992) "Comparison of the Locations of Homologous Fowlpox and Vaccinia Virus Genes Reveals Major Genome Reorganization", Journal of General Virology 73:2662–2668 (Ex. 75).
Calvert, J.G. et al. (1992) "Identification and Functional Analysis of the Fowlpox Virus Homolog of the Vaccinia Virus P37k Major Envelope Antigen Gene", Virology 191:783–792 (Ex. 76).
Beard, C.W. et al. (1992) "Effect of Route of Administration of the Efficacy of A Recombinant Fowlpox Virus Against H5n2 Avain Influenza", Avain Dis 36:1052–1055 (Ex. 77).
Baxby, D. and Paoletti, E. (1992) "Potential Use of Non–Replicating Vectors as Recombinant Vaccines", Vaccine 10:8–9 (Ex. 78).
Ogawa, R. et al. (1993) "Insertional Inactivation of a Fowlpox Virus Homologue of the Vaccinia Virus F12L Gene Inhibits the Release of Enveloped Virions", Journal of General Virology 74:55–64 (Ex. 79).

Edbauer et al. "Protection of Chickens with a Recombinant Fowlpox Virus expressing the Newcastle Disease Virus Hemagglutinin–Neuraminidase Gene". Virology. vol. 79:901–904, 1990.
Cochran et al. J. Virol. 54(1):30–37 1985.
Boursnell et al. J. Gen. Virol. 71:621–628 1990.
Earl et al. J. Virol. 64(5):2448–51 1990.
Davison et al. J. Mol. Biol. 210:771–784 1989.
Davison et al. J. Mol. Biol. 210:749–769.
Umino et al. Arch. Virol. 94(1–2):97–107 1987 (see abstract).
Taylor et al. J. Virol. 64(4):1441–1450 1990 (see abstract).

SEQUENCE LISTING

```
(1) GENERAL INFORMATION:

   (iii) NUMBER OF SEQUENCES: 20

(2) INFORMATION FOR SEQ ID NO:1:

     (i) SEQUENCE CHARACTERISTICS:
          (A) LENGTH: 28 base pairs
          (B) TYPE: nucleic acid
          (C) STRANDEDNESS: double
          (D) TOPOLOGY: linear

    (ii) MOLECULE TYPE: DNA (genomic)
```

-continued (iii) HYPOTHETICAL: NO (iv) ANTI-SENSE: NO (xi) SEQUENCE DESCRIPTION: SEQ ID NO:1:

```
CATAAGGCGG CCGCGGCCCT CGAGGCCA                                   28
```

(2) INFORMATION FOR SEQ ID NO:2:

(i) SEQUENCE CHARACTERISTICS:
(A) LENGTH: 28 base pairs
(B) TYPE: nucleic acid
(C) STRANDEDNESS: double
(D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:2:

```
CATAATGGCC TCGAGGGCCG CGGCCGCC                                   28
```

(2) INFORMATION FOR SEQ ID NO:3:

(i) SEQUENCE CHARACTERISTICS:
(A) LENGTH: 1507 base pairs
(B) TYPE: nucleic acid
(C) STRANDEDNESS: double
(D) TOPOLOGY: linear (ii) MOLECULE TYPE: DNA (genomic)

(iii) HYPOTHETICAL: NO (iv) ANTI-SENSE: NO (ix) FEATURE:
(A) NAME/KEY: CDS
(B) LOCATION: 260..1411

(xi) SEQUENCE DESCRIPTION: SEQ ID NO:3:

```
CTACTTCATA AAAAGTTTAA ACCTTCCGAA AGATTTTTGG ATAAAAGTAG AGAACTCGCA     60

TTGCGATTAT GCTCTAGGAC AATCCTGTAA AGTGTCTCGA TCTTAGCATA TAGATAAATG    120

TTTGAACTAA TATCCTAAAG CCTGTATGTA ACAGTTGGTG CCTATTGAAA GATACTGATT    180

ATCAAGGAGA AGAATAATAT AAATCGTAAA AATAATACTT ATTATATAAT ATAATGTATA    240

ATAATATACA AAAACAGCC ATG ATA CGT ATT ATA ATA TTA TCG TTA TTA TTT     292
                     Met Ile Arg Ile Ile Ile Leu Ser Leu Leu Phe
                      1               5                  10

ATT AAC GTA ACA ACA GAT AGT CAA GAA TCT TCA AAA AAT ATA CAA AAT     340
Ile Asn Val Thr Thr Asp Ser Gln Glu Ser Ser Lys Asn Ile Gln Asn
            15                  20                  25

GTA TTG CAC GTT ACA GAA TAT AGT AGA ACT GGT GTA ACA GCT TGC TCG     388
Val Leu His Val Thr Glu Tyr Ser Arg Thr Gly Val Thr Ala Cys Ser
        30                  35                  40

TTA CAT TGT TTT GAT CGT TCC AAA GGT TTA GAT CAA CCA AAA ACA TTT     436
Leu His Cys Phe Asp Arg Ser Lys Gly Leu Asp Gln Pro Lys Thr Phe
    45                  50                  55

ATC CTG CCT GGT AAA TAT AGC AAT AAC AGT ATA AAA CTA GAA GTA GCT     484
Ile Leu Pro Gly Lys Tyr Ser Asn Asn Ser Ile Lys Leu Glu Val Ala
 60                  65                  70                  75

ATT GAT ACA TAT AAA AAA GAT AGC GAC TTC AGT TAT TCT CAC CCA TGT     532
Ile Asp Thr Tyr Lys Lys Asp Ser Asp Phe Ser Tyr Ser His Pro Cys
                80                  85                  90
```

-continued

```
CAA ATA TTC CAG TTC TGT GTG TCT GGT AAT TTT AGT GGT AAA CGG TTC      580
Gln Ile Phe Gln Phe Cys Val Ser Gly Asn Phe Ser Gly Lys Arg Phe
             95                 100                 105

GAT CAT TAT CTA TAT GGG TAT ACA ATT TCC GGA TTT ATA GAT ATT GCT      628
Asp His Tyr Leu Tyr Gly Tyr Thr Ile Ser Gly Phe Ile Asp Ile Ala
        110                 115                 120

CCA AAA TAT TAT AGC GGT ATG TCT ATA AGT ACT ATT ACT GTT ATG CCA      676
Pro Lys Tyr Tyr Ser Gly Met Ser Ile Ser Thr Ile Thr Val Met Pro
    125                 130                 135

TTA CAA GAA GGA TCA TTA AAG CAT GAT GAT GCC GAT GAC TAT GAC TAC      724
Leu Gln Glu Gly Ser Leu Lys His Asp Asp Ala Asp Asp Tyr Asp Tyr
140                 145                 150                 155

GAT GAT GAT TGT GTT CCT TAT AAA GAA ACC CAG CCT CGA CAT ATG CCA      772
Asp Asp Asp Cys Val Pro Tyr Lys Glu Thr Gln Pro Arg His Met Pro
                160                 165                 170

GAA TCG GTA ATA AAA GAA GGA TGT AAA CCC ATT CCA CTA CCA AGG TAT      820
Glu Ser Val Ile Lys Glu Gly Cys Lys Pro Ile Pro Leu Pro Arg Tyr
            175                 180                 185

GAT GAA AAT GAC GAT CCT ACT TGT ATT ATG TAT TGG GAT CAC TCG TGG      868
Asp Glu Asn Asp Asp Pro Thr Cys Ile Met Tyr Trp Asp His Ser Trp
        190                 195                 200

GAT AAT TAC TGT AAT GTT GGA TTT TTT AAT TCT CTA CAG AGT GAT CAC      916
Asp Asn Tyr Cys Asn Val Gly Phe Phe Asn Ser Leu Gln Ser Asp His
    205                 210                 215

AAT CCT CTG GTT TTT CCG TTA ACA AGT TAT TCT GAT ATA AAC AAT GCA      964
Asn Pro Leu Val Phe Pro Leu Thr Ser Tyr Ser Asp Ile Asn Asn Ala
220                 225                 230                 235

TTT CAT GCT TTT CAA TCA TCT TAT TGT AGA TCA CTA GGC TTT AAC CAA     1012
Phe His Ala Phe Gln Ser Ser Tyr Cys Arg Ser Leu Gly Phe Asn Gln
                240                 245                 250

TCA TAC AGT GTA TGC GTA TCT ATA GGT GAT ACA CCA TTT GAG GTT ACG     1060
Ser Tyr Ser Val Cys Val Ser Ile Gly Asp Thr Pro Phe Glu Val Thr
            255                 260                 265

TAT CAT AGT TAT GAA AGT GTT ACT GTT GAT CAG TTA TTA CAA GAA ATT     1108
Tyr His Ser Tyr Glu Ser Val Thr Val Asp Gln Leu Leu Gln Glu Ile
        270                 275                 280

AAA ACA CTA TAT GGA GAA GAT GCT GTA TAT GGA TTA CCG TTT AGA AAT     1156
Lys Thr Leu Tyr Gly Glu Asp Ala Val Tyr Gly Leu Pro Phe Arg Asn
    285                 290                 295

ATA ACT ATA AGG GCG CGT ACA CGG ATT CAA AGT TTA CCT CTT ACT AAC     1204
Ile Thr Ile Arg Ala Arg Thr Arg Ile Gln Ser Leu Pro Leu Thr Asn
300                 305                 310                 315

AAT ACC TGT ATC CCT AAA CAA GAC GAT GCT GAT GAT GTT GAC GAT GCT     1252
Asn Thr Cys Ile Pro Lys Gln Asp Asp Ala Asp Asp Val Asp Asp Ala
                320                 325                 330

GAT GAT GTT GAC GAT GCT GAT GAT GCT GAC GAT GAT GAT GAT TAC GAG     1300
Asp Asp Val Asp Asp Ala Asp Asp Ala Asp Asp Asp Asp Asp Tyr Glu
            335                 340                 345

TTA TAT GTA GAA ACT ACA CCA AGA GTG CCA ACA GCG AGA AAA AAA CCC     1348
Leu Tyr Val Glu Thr Thr Pro Arg Val Pro Thr Ala Arg Lys Lys Pro
        350                 355                 360

GTT ACA GAA GAA TAT AAT GAT ATA TTT AGT AGT TTT GAT AAT TTT GAC     1396
Val Thr Glu Glu Tyr Asn Asp Ile Phe Ser Ser Phe Asp Asn Phe Asp
    365                 370                 375

ATG AAA AAG AAA TAAGACATAT TTTATTAAAT CAAAAGTCT GTCGAACTTT          1448
Met Lys Lys Lys
380

TAGTGTTTAA CCTATATCGA TTTATGATTT TTCCATGATG ATCCAGGCTA TGACTGACT    1507
```

-continued (2) INFORMATION FOR SEQ ID NO:4:

(i) SEQUENCE CHARACTERISTICS:
(A) LENGTH: 383 amino acids
(B) TYPE: amino acid
(D) TOPOLOGY: linear (ii) MOLECULE TYPE: protein (xi) SEQUENCE DESCRIPTION: SEQ ID NO:4:

```
Met Ile Arg Ile Ile Ile Leu Ser Leu Leu Phe Ile Asn Val Thr Thr
  1               5                  10                  15

Asp Ser Gln Glu Ser Ser Lys Asn Ile Gln Asn Val Leu His Val Thr
             20                  25                  30

Glu Tyr Ser Arg Thr Gly Val Thr Ala Cys Ser Leu His Cys Phe Asp
         35                  40                  45

Arg Ser Lys Gly Leu Asp Gln Pro Lys Thr Phe Ile Leu Pro Gly Lys
     50                  55                  60

Tyr Ser Asn Asn Ser Ile Lys Leu Glu Val Ala Ile Asp Thr Tyr Lys
 65                  70                  75                  80

Lys Asp Ser Asp Phe Ser Tyr Ser His Pro Cys Gln Ile Phe Gln Phe
                 85                  90                  95

Cys Val Ser Gly Asn Phe Ser Gly Lys Arg Phe Asp His Tyr Leu Tyr
            100                 105                 110

Gly Tyr Thr Ile Ser Gly Phe Ile Asp Ile Ala Pro Lys Tyr Tyr Ser
        115                 120                 125

Gly Met Ser Ile Ser Thr Ile Thr Val Met Pro Leu Gln Glu Gly Ser
    130                 135                 140

Leu Lys His Asp Asp Ala Asp Asp Tyr Asp Tyr Asp Asp Asp Cys Val
145                 150                 155                 160

Pro Tyr Lys Glu Thr Gln Pro Arg His Met Pro Glu Ser Val Ile Lys
                165                 170                 175

Glu Gly Cys Lys Pro Ile Pro Leu Pro Arg Tyr Asp Glu Asn Asp Asp
            180                 185                 190

Pro Thr Cys Ile Met Tyr Trp Asp His Ser Trp Asp Asn Tyr Cys Asn
        195                 200                 205

Val Gly Phe Phe Asn Ser Leu Gln Ser Asp His Asn Pro Leu Val Phe
    210                 215                 220

Pro Leu Thr Ser Tyr Ser Asp Ile Asn Asn Ala Phe His Ala Phe Gln
225                 230                 235                 240

Ser Ser Tyr Cys Arg Ser Leu Gly Phe Asn Gln Ser Tyr Ser Val Cys
                245                 250                 255

Val Ser Ile Gly Asp Thr Pro Phe Glu Val Thr Tyr His Ser Tyr Glu
            260                 265                 270

Ser Val Thr Val Asp Gln Leu Leu Gln Glu Ile Lys Thr Leu Tyr Gly
        275                 280                 285

Glu Asp Ala Val Tyr Gly Leu Pro Phe Arg Asn Ile Thr Ile Arg Ala
    290                 295                 300

Arg Thr Arg Ile Gln Ser Leu Pro Leu Thr Asn Asn Thr Cys Ile Pro
305                 310                 315                 320

Lys Gln Asp Asp Ala Asp Asp Val Asp Asp Ala Asp Asp Val Asp Asp
                325                 330                 335

Ala Asp Asp Ala Asp Asp Asp Asp Asp Tyr Glu Leu Tyr Val Glu Thr
            340                 345                 350

Thr Pro Arg Val Pro Thr Ala Arg Lys Lys Pro Val Thr Glu Glu Tyr
```

-continued

```
        355                 360                 365

Asn Asp Ile Phe Ser Ser Phe Asp Asn Phe Asp Met Lys Lys Lys
    370                 375                 380
```

(2) INFORMATION FOR SEQ ID NO:5:

(i) SEQUENCE CHARACTERISTICS:
(A) LENGTH: 2849 base pairs
(B) TYPE: nucleic acid
(C) STRANDEDNESS: double
(D) TOPOLOGY: linear (ii) MOLECULE TYPE: DNA (genomic)

(iii) HYPOTHETICAL: NO (iv) ANTI-SENSE: NO (ix) FEATURE:
(A) NAME/KEY: CDS
(B) LOCATION: 300..1568

(ix) FEATURE:
(A) NAME/KEY: CDS
(B) LOCATION: complement (1685..2848)

(xi) SEQUENCE DESCRIPTION: SEQ ID NO:5:

```
AAGCCAGTTT GAATTCAATA TTCATCGCCG ATAGTTGGTA GAAATACTAT TCATGAAATT      60

TACCTTCTTC CGTGGCTTAA AAACTTATTG TATGTACCAT TCATTATAAG ATCTGATACT     120

ATCGGCATCT TCTATTTTCC GAGTTTTTTA CATCTGGTTA CTAGTATCCA TGTTCGTCTA     180

ATAAGAGGGA AGGAATATAT CTATCTACAT AAACATCATA AGGTTCTTTG ATAGATTTAT     240

ATCGCTAATA AAATATAAAT AATAATTAAA GATTTTATGA TATATCGAGC TTTGCAAAA      299

ATG TCT GTT GAT TGG CGT ACA GAA ATC TAT TCG GGT GAT ATA TCC CTA       347
Met Ser Val Asp Trp Arg Thr Glu Ile Tyr Ser Gly Asp Ile Ser Leu
  1               5                  10                  15

GTA GAA AAA CTT ATA AAG AAT AAA GGT AAT TGC ATC AAT ATA TCT GTA       395
Val Glu Lys Leu Ile Lys Asn Lys Gly Asn Cys Ile Asn Ile Ser Val
             20                  25                  30

GAG GAA ACA ACA ACT CCG TTA ATA GAC GCT ATA AGA ACC GGA AAT GCC       443
Glu Glu Thr Thr Thr Pro Leu Ile Asp Ala Ile Arg Thr Gly Asn Ala
         35                  40                  45

AAA ATA GTA GAA CTA TTT ATC AAG CAC GGA GCG CAA GTT AAT CAT GTA       491
Lys Ile Val Glu Leu Phe Ile Lys His Gly Ala Gln Val Asn His Val
     50                  55                  60

AAT ACT AAA ATT CCT AAT CCC TTG TTA ACA GCT ATC AAA ATA GGA TCA       539
Asn Thr Lys Ile Pro Asn Pro Leu Leu Thr Ala Ile Lys Ile Gly Ser
 65                  70                  75                  80

CAC GAT ATA GTA AAA CTG CTG TTG ATT AAC GGA GTT GAT ACT TCT ATT       587
His Asp Ile Val Lys Leu Leu Leu Ile Asn Gly Val Asp Thr Ser Ile
                 85                  90                  95

TTG CCA GTC CCC TGC ATA AAT AAA GAA ATG ATA AAA ACT ATA TTA GAT       635
Leu Pro Val Pro Cys Ile Asn Lys Glu Met Ile Lys Thr Ile Leu Asp
            100                 105                 110

AGT GGT GTG AAA GTA AAC ACA AAA AAT GCT AAA TCT AAA ACT TTC TTG       683
Ser Gly Val Lys Val Asn Thr Lys Asn Ala Lys Ser Lys Thr Phe Leu
        115                 120                 125

CAT TAC GCG ATT AAG AAT AAT GAC TTA GAG GTT ATC AAA ATG CTT TTT       731
His Tyr Ala Ile Lys Asn Asn Asp Leu Glu Val Ile Lys Met Leu Phe
    130                 135                 140

GAG TAT GGA GCT GAT GTT AAT ATA AAA GAT GAT AAC ATA TGT TAT TCT       779
Glu Tyr Gly Ala Asp Val Asn Ile Lys Asp Asp Asn Ile Cys Tyr Ser
145                 150                 155                 160
```

-continued

```
ATA CAC ATA GCT ACT AGG AGT AAT TCA TAT GAA ATC ATA AAA TTA CTA      827
Ile His Ile Ala Thr Arg Ser Asn Ser Tyr Glu Ile Ile Lys Leu Leu
                165                 170                 175

TTA GAA AAA GGT GCT TAT GCA AAC GTA AAA GAC AAT TAT GGT AAT TCT      875
Leu Glu Lys Gly Ala Tyr Ala Asn Val Lys Asp Asn Tyr Gly Asn Ser
            180                 185                 190

CCG TTA CAT AAC GCG GCT AAA TAT GGC GAT TAT GCT TGT ATT AAA TTA      923
Pro Leu His Asn Ala Ala Lys Tyr Gly Asp Tyr Ala Cys Ile Lys Leu
        195                 200                 205

GTT TTA GAC CAT ACT AAT AAC ATA AGC AAT AAG TGC AAC AAC GGT GTT      971
Val Leu Asp His Thr Asn Asn Ile Ser Asn Lys Cys Asn Asn Gly Val
    210                 215                 220

ACA CCG TTA CAT AAC GCT ATA CTA TAT AAT AGA TCT GCC GTA GAA TTA     1019
Thr Pro Leu His Asn Ala Ile Leu Tyr Asn Arg Ser Ala Val Glu Leu
225                 230                 235                 240

CTG ATT AAC AAT CGA TCT ATT AAT GAT ACG GAT GTA GAC GGA TAT ACT     1067
Leu Ile Asn Asn Arg Ser Ile Asn Asp Thr Asp Val Asp Gly Tyr Thr
                245                 250                 255

CCA CTA CAT TAT GCT TTG CAA CCT CCG TGT AGT ATA GAT ATT ATA GAT     1115
Pro Leu His Tyr Ala Leu Gln Pro Pro Cys Ser Ile Asp Ile Ile Asp
            260                 265                 270

ATA CTA CTA TAT AAC AAC GCC GAT ATA TCT ATA AAA GAT AAT AAC GGA     1163
Ile Leu Leu Tyr Asn Asn Ala Asp Ile Ser Ile Lys Asp Asn Asn Gly
        275                 280                 285

CGC AAT CCT ATC GAT ACG GCG TTT AAG TAT ATT AAC AGA GAT AGC GTT     1211
Arg Asn Pro Ile Asp Thr Ala Phe Lys Tyr Ile Asn Arg Asp Ser Val
    290                 295                 300

ATA AAA GAA CTT CTC CGA AAC GCC GTG TTA ATT AAC GAG GTC GGT AAA     1259
Ile Lys Glu Leu Leu Arg Asn Ala Val Leu Ile Asn Glu Val Gly Lys
305                 310                 315                 320

TTA AAA GAT ACT ACT ATC TTA GAA CAC AAA GAA ATA AAA GAC AAT ACC     1307
Leu Lys Asp Thr Thr Ile Leu Glu His Lys Glu Ile Lys Asp Asn Thr
                325                 330                 335

GTG TTT TCA AAC TTT GTG TAC GAA TGT AAT GAA GAA ATT AAA AAA ATG     1355
Val Phe Ser Asn Phe Val Tyr Glu Cys Asn Glu Glu Ile Lys Lys Met
            340                 345                 350

AAG AAA ACT AAA TGT GTC GGT GAC TAT AGT ATG TTT GAC GTA TAC ATG     1403
Lys Lys Thr Lys Cys Val Gly Asp Tyr Ser Met Phe Asp Val Tyr Met
        355                 360                 365

ATA AGG TAT AAA CAC AAA TAT GAC GGT AAT AAG GAT AGT ATT AAA GAC     1451
Ile Arg Tyr Lys His Lys Tyr Asp Gly Asn Lys Asp Ser Ile Lys Asp
    370                 375                 380

TAT TTG CGT TGT CTT GAT GAT AAT AGT ACT CGT ATG TTA AAA ACT ATA     1499
Tyr Leu Arg Cys Leu Asp Asp Asn Ser Thr Arg Met Leu Lys Thr Ile
385                 390                 395                 400

GAT ATT AAT GAA TTT CCT ATA TAT TCT ATG TAT CTC GTA AGA TGC CTA     1547
Asp Ile Asn Glu Phe Pro Ile Tyr Ser Met Tyr Leu Val Arg Cys Leu
                405                 410                 415

TAT GAT ATG GTA ATA TAT TAAAAGAAAT GGGCTCTTGC ATACATAATC            1595
Tyr Asp Met Val Ile Tyr
            420

GGTATAAAAA ATAACGAAAT TATTAGCGGT TACATATCTT ACGGCGGCCG CGGCCCTCGA   1655

GGCCAGTAGC TCAGTATTTC CTATAAACTC TAATATTGAG AGTTTGATAT CCGGAGAAGT   1715

TTAGACCAAC CGCTAGAATC TAATATTTCA TCTAATTTTG ATCTACTTTT TTCTAATATT   1775

TTATGTCTAT TACTGGCTAA GGATATGGAA GTTTTAAGAC GATCTCCGTA ATTATAGAAA   1835

TAGTAAGTAT TAATTTCCTT TATTATAGGA TTATTTACTA AGTGATGTAA CAGGTTCATG   1895
```

-continued

```
TTTTTACTAA TAACGAATAT ATCTAAAGAG TAAAACATAT TAATACGAAT TTTAGATATA   1955

TCTTTTAGTT CTTCCTTACA ACTCAACCAA ATACTTTTAA ACGTATCATC GCTTTGAATA   2015

ATTTCTCTCA AGGGGTTTAC TTCACTTCTG ATATCGTGAC GTATAAAATC TTGTATACAT   2075

ATATGTGCTA TGATATATCT AAAAGAAAAC ATATTACTGT TAAGGCTCTT ATCGATGACC   2135

CTACTATCTC TAAGTTCAGC ACCATAATGT AATAATATAT TTACTATACC ATGATATTCT   2195

AATGCTATTA ATAAAGGATA TTGATTCCTT ATGTTAATAG CATTTACATC CGCTCCGTTA   2255

TCTAATAACA TTTTTATAAC TTCTGGTTTA CAATTCTTTT TACACGCATA ATGCAACGGA   2315

GTAGATAAGT ATTTGTTTTT AGAATTAACA TTAGCTCCTC TATCTATGAG CGTTTTTACA   2375

CTCATATACG GATTTGTTCC ATATAAGGCA AAATGTAAAA CCGTTCCTAT CTTCTGCGAT   2435

AACGCTTCTA TATCGGCCCC GTAATCTAAA AGAGTGTTTA TGATAACTAC ATTGTTTCTT   2495

ACAGCGGCAT AATGAATAGG CGTCTTGTCA CAATAATCTC TAGCATTTAC GTTCGCTCCC   2555

AATTCTAACA ACGTTATAAC TGTATCTTTA TATCTATCTA GAGTAGAGGC TTGATGTAAT   2615

GGAGTGATAT ACAGACTATC AGCGGCGTTA ACATCTGCAC CCCGCATTAT TAAAGTTCTA   2675

ATGTTTTCTG TATCGTATCC ATTCTTAGCC ATGAGATACA GAGGAGTTTC TCCTTTAATG   2735

TTTTTAGCGT TAACATCTAT TCCTCTTTCC AATAACTTGG GTACTAGTCT ACTTAACGAA   2795

GGTGCTTGTA CCGTGTAATG CAAAGGAGTA TTCTTATAAA CATCTATAGA ATTC         2849
```

(2) INFORMATION FOR SEQ ID NO:6:

(i) SEQUENCE CHARACTERISTICS:
(A) LENGTH: 422 amino acids
(B) TYPE: amino acid
(D) TOPOLOGY: linear (ii) MOLECULE TYPE: protein (xi) SEQUENCE DESCRIPTION: SEQ ID NO:6:

```
Met Ser Val Asp Trp Arg Thr Glu Ile Tyr Ser Gly Asp Ile Ser Leu
  1               5                  10                  15

Val Glu Lys Leu Ile Lys Asn Lys Gly Asn Cys Ile Asn Ile Ser Val
             20                  25                  30

Glu Glu Thr Thr Thr Pro Leu Ile Asp Ala Ile Arg Thr Gly Asn Ala
         35                  40                  45

Lys Ile Val Glu Leu Phe Ile Lys His Gly Ala Gln Val Asn His Val
     50                  55                  60

Asn Thr Lys Ile Pro Asn Pro Leu Leu Thr Ala Ile Lys Ile Gly Ser
 65                  70                  75                  80

His Asp Ile Val Lys Leu Leu Leu Ile Asn Gly Val Asp Thr Ser Ile
                 85                  90                  95

Leu Pro Val Pro Cys Ile Asn Lys Glu Met Ile Lys Thr Ile Leu Asp
            100                 105                 110

Ser Gly Val Lys Val Asn Thr Lys Asn Ala Lys Ser Lys Thr Phe Leu
        115                 120                 125

His Tyr Ala Ile Lys Asn Asn Asp Leu Glu Val Ile Lys Met Leu Phe
    130                 135                 140

Glu Tyr Gly Ala Asp Val Asn Ile Lys Asp Asp Asn Ile Cys Tyr Ser
145                 150                 155                 160

Ile His Ile Ala Thr Arg Ser Asn Ser Tyr Glu Ile Ile Lys Leu Leu
                165                 170                 175

Leu Glu Lys Gly Ala Tyr Ala Asn Val Lys Asp Asn Tyr Gly Asn Ser
            180                 185                 190
```

-continued

Pro Leu His Asn Ala Ala Lys Tyr Gly Asp Tyr Ala Cys Ile Lys Leu
195 200 205

Val Leu Asp His Thr Asn Asn Ile Ser Asn Lys Cys Asn Asn Gly Val
210 215 220

Thr Pro Leu His Asn Ala Ile Leu Tyr Asn Arg Ser Ala Val Glu Leu
225 230 235 240

Leu Ile Asn Asn Arg Ser Ile Asn Asp Thr Asp Val Asp Gly Tyr Thr
245 250 255

Pro Leu His Tyr Ala Leu Gln Pro Pro Cys Ser Ile Asp Ile Ile Asp
260 265 270

Ile Leu Leu Tyr Asn Asn Ala Asp Ile Ser Ile Lys Asp Asn Asn Gly
275 280 285

Arg Asn Pro Ile Asp Thr Ala Phe Lys Tyr Ile Asn Arg Asp Ser Val
290 295 300

Ile Lys Glu Leu Leu Arg Asn Ala Val Leu Ile Asn Glu Val Gly Lys
305 310 315 320

Leu Lys Asp Thr Thr Ile Leu Glu His Lys Glu Ile Lys Asp Asn Thr
325 330 335

Val Phe Ser Asn Phe Val Tyr Glu Cys Asn Glu Glu Ile Lys Lys Met
340 345 350

Lys Lys Thr Lys Cys Val Gly Asp Tyr Ser Met Phe Asp Val Tyr Met
355 360 365

Ile Arg Tyr Lys His Lys Tyr Asp Gly Asn Lys Asp Ser Ile Lys Asp
370 375 380

Tyr Leu Arg Cys Leu Asp Asp Asn Ser Thr Arg Met Leu Lys Thr Ile
385 390 395 400

Asp Ile Asn Glu Phe Pro Ile Tyr Ser Met Tyr Leu Val Arg Cys Leu
405 410 415

Tyr Asp Met Val Ile Tyr
420

(2) INFORMATION FOR SEQ ID NO:7:

(i) SEQUENCE CHARACTERISTICS:
(A) LENGTH: 387 amino acids
(B) TYPE: amino acid
(D) TOPOLOGY: linear (ii) MOLECULE TYPE: protein (xi) SEQUENCE DESCRIPTION: SEQ ID NO:7:

Asn Ser Ile Asp Val Tyr Lys Asn Thr Pro Leu His Tyr Thr Val Gln
1 5 10 15

Ala Pro Ser Leu Ser Arg Leu Val Pro Lys Leu Leu Glu Arg Gly Ile
20 25 30

Asp Val Asn Ala Lys Asn Ile Lys Gly Glu Thr Pro Leu Tyr Leu Met
35 40 45

Ala Lys Asn Gly Tyr Asp Thr Glu Asn Ile Arg Thr Leu Ile Met Arg
50 55 60

Gly Ala Asp Val Asn Ala Ala Asp Ser Leu Tyr Ile Thr Pro Leu His
65 70 75 80

Gln Ala Ser Thr Leu Asp Arg Tyr Lys Asp Thr Val Ile Thr Leu Leu
85 90 95

Glu Leu Gly Ala Asn Val Asn Ala Arg Asp Tyr Cys Asp Lys Thr Pro
100 105 110

```
Ile His Tyr Ala Ala Val Arg Asn Asn Val Val Ile Ile Asn Thr Leu
        115                 120                 125

Leu Asp Tyr Gly Ala Asp Ile Glu Ala Leu Ser Gln Lys Ile Gly Thr
130                 135                 140

Val Leu His Phe Ala Leu Tyr Gly Thr Asn Pro Tyr Met Ser Val Lys
145                 150                 155                 160

Thr Leu Ile Asp Arg Gly Ala Asn Val Asn Ser Lys Asn Lys Tyr Leu
                165                 170                 175

Ser Thr Pro Leu His Tyr Ala Cys Lys Lys Asn Cys Lys Pro Glu Val
            180                 185                 190

Ile Lys Met Leu Leu Asp Asn Gly Ala Asp Val Asn Ala Ile Asn Ile
        195                 200                 205

Arg Asn Gln Tyr Pro Leu Leu Ile Ala Leu Glu Tyr His Gly Ile Val
210                 215                 220

Asn Ile Leu Leu His Tyr Gly Ala Glu Leu Arg Asp Ser Arg Val Ile
225                 230                 235                 240

Asp Lys Ser Leu Asn Ser Asn Met Phe Ser Phe Arg Tyr Ile Ile Ala
                245                 250                 255

His Ile Cys Ile Gln Asp Phe Ile Arg His Asp Ile Arg Ser Glu Val
            260                 265                 270

Asn Pro Leu Arg Glu Ile Ile Gln Ser Asp Asp Thr Phe Lys Ser Ile
        275                 280                 285

Trp Leu Ser Cys Lys Glu Glu Leu Lys Asp Ile Ser Lys Ile Arg Ile
290                 295                 300

Asn Met Phe Tyr Ser Leu Asp Ile Phe Val Ile Ser Lys Asn Met Asn
305                 310                 315                 320

Leu Leu His His Leu Val Asn Asn Pro Ile Ile Lys Glu Ile Asn Thr
                325                 330                 335

Tyr Tyr Phe Tyr Asn Tyr Gly Asp Arg Leu Lys Thr Ser Ile Ser Leu
            340                 345                 350

Ala Ser Asn Arg His Lys Ile Leu Glu Lys Ser Arg Ser Lys Leu Asp
        355                 360                 365

Glu Ile Leu Asp Ser Ser Gly Trp Ser Lys Leu Leu Arg Ile Ser Asn
370                 375                 380

Ser Gln Tyr
385

(2) INFORMATION FOR SEQ ID NO:8:

    (i) SEQUENCE CHARACTERISTICS:
        (A) LENGTH: 40 base pairs
        (B) TYPE: nucleic acid
        (C) STRANDEDNESS: double
        (D) TOPOLOGY: linear

   (ii) MOLECULE TYPE: DNA (genomic)

  (iii) HYPOTHETICAL: NO

   (iv) ANTI-SENSE: NO

   (xi) SEQUENCE DESCRIPTION: SEQ ID NO:8:

AAAAATTGAA AAACTATTCT AATTTATTGC ACGGAGATCT                      40

(2) INFORMATION FOR SEQ ID NO:9:

    (i) SEQUENCE CHARACTERISTICS:
        (A) LENGTH: 32 base pairs
        (B) TYPE: nucleic acid
```

-continued (C) STRANDEDNESS: double
(D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:9:

AATTTCATTT TGTTTTTTTC TATGCTATAA AT 32

(2) INFORMATION FOR SEQ ID NO:10:

(i) SEQUENCE CHARACTERISTICS:
(A) LENGTH: 37 base pairs
(B) TYPE: nucleic acid
(C) STRANDEDNESS: double
(D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:10:

GTATCCTAAA ATTGAATTGT AATTATCGAT AATAAAT 37

(2) INFORMATION FOR SEQ ID NO:11:

(i) SEQUENCE CHARACTERISTICS:
(A) LENGTH: 42 base pairs
(B) TYPE: nucleic acid
(C) STRANDEDNESS: double
(D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:11:

TTTTTTTTTT TTTTTTTTTT GGCATATAAA TGAATTCGGA TC 42

(2) INFORMATION FOR SEQ ID NO:12:

(i) SEQUENCE CHARACTERISTICS:
(A) LENGTH: 4177 base pairs
(B) TYPE: nucleic acid
(C) STRANDEDNESS: double
(D) TOPOLOGY: linear (ii) MOLECULE TYPE: DNA (genomic)

(iii) HYPOTHETICAL: NO (iv) ANTI-SENSE: NO (ix) FEATURE:
(A) NAME/KEY: CDS
(B) LOCATION: 115..1860

(ix) FEATURE:
(A) NAME/KEY: CDS
(B) LOCATION: 2095..3756

(xi) SEQUENCE DESCRIPTION: SEQ ID NO:12:

CATACTGGCC TCGAGGGCCG CGGCCGCCTG CAGGTCGACT CTAGAAAAAA TTGAAAAACT 60

ATTCTAATTT ATTGCACGGA GATCTTTTTT TTTTTTTTTT TTTTTGGCAT ATAA ATG 117

-continued

```
                                                         Met
                                                           1

AAT TCG GAT CCG GAC CGC GCC GTT AGC CAA GTT GCG TTA GAG AAT GAT       165
Asn Ser Asp Pro Asp Arg Ala Val Ser Gln Val Ala Leu Glu Asn Asp
                  5                  10                  15

GAA AGA GAG GCA AAA AAT ACA TGG CGC TTG ATA TTC CGG ATT GCA ATC       213
Glu Arg Glu Ala Lys Asn Thr Trp Arg Leu Ile Phe Arg Ile Ala Ile
         20                  25                  30

TTA TTC TTA ACA GTA GTG ACC TTG GCT ATA TCT GTA GCC TCC CTT TTA       261
Leu Phe Leu Thr Val Val Thr Leu Ala Ile Ser Val Ala Ser Leu Leu
     35                  40                  45

TAT AGC ATG GGG GCT AGC ACA CCT AGC GAT CTT GTA GGC ATA CCG ACT       309
Tyr Ser Met Gly Ala Ser Thr Pro Ser Asp Leu Val Gly Ile Pro Thr
 50                  55                  60                  65

AGG ATT TCC AGG GCA GAA GAA AAG ATT ACA TCT ACA CTT GGT TCC AAT       357
Arg Ile Ser Arg Ala Glu Glu Lys Ile Thr Ser Thr Leu Gly Ser Asn
                 70                  75                  80

CAA GAT GTA GTA GAT AGG ATA TAT AAG CAA GTG GCC CTT GAG TCT CCA       405
Gln Asp Val Val Asp Arg Ile Tyr Lys Gln Val Ala Leu Glu Ser Pro
             85                  90                  95

TTG GCA TTG TTA AAT ACT GAG ACC ACA ATT ATG AAC GCA ATA ACA TCT       453
Leu Ala Leu Leu Asn Thr Glu Thr Thr Ile Met Asn Ala Ile Thr Ser
        100                 105                 110

CTC TCT TAT CAG ATT AAT GGA GCT GCA AAC AAC AGC GGG TGG GGG GCA       501
Leu Ser Tyr Gln Ile Asn Gly Ala Ala Asn Asn Ser Gly Trp Gly Ala
    115                 120                 125

CCT ATT CAT GAC CCA GAT TAT ATA GGG GGG ATA GGC AAA GAA CTC ATT       549
Pro Ile His Asp Pro Asp Tyr Ile Gly Gly Ile Gly Lys Glu Leu Ile
130                 135                 140                 145

GTA GAT GAT GCT AGT GAT GTC ACA TCA TTC TAT CCC TCT GCA TTT CAA       597
Val Asp Asp Ala Ser Asp Val Thr Ser Phe Tyr Pro Ser Ala Phe Gln
                150                 155                 160

GAA CAT CTG AAT TTT ATC CCG GCG CCT ACT ACA GGA TCA GGT TGC ACT       645
Glu His Leu Asn Phe Ile Pro Ala Pro Thr Thr Gly Ser Gly Cys Thr
            165                 170                 175

CGA ATA CCC TCA TTT GAC ATG AGT GCT ACC CAT TAC TGC TAC ACC CAT       693
Arg Ile Pro Ser Phe Asp Met Ser Ala Thr His Tyr Cys Tyr Thr His
        180                 185                 190

AAT GTA ATA TTG TCT GGA TGC AGA GAT CAC TCA CAC TCA CAT CAG TAT       741
Asn Val Ile Leu Ser Gly Cys Arg Asp His Ser His Ser His Gln Tyr
    195                 200                 205

TTA GCA CTT GGT GTG CTC CGG ACA TCT GCA ACA GGG AGG GTA TTC TTT       789
Leu Ala Leu Gly Val Leu Arg Thr Ser Ala Thr Gly Arg Val Phe Phe
210                 215                 220                 225

TCT ACT CTG CGT TCC ATC AAC CTG GAC GAC ACC CAA AAT CGG AAG TCT       837
Ser Thr Leu Arg Ser Ile Asn Leu Asp Asp Thr Gln Asn Arg Lys Ser
                230                 235                 240

TGC AGT GTG AGT GCA ACT CCC CTG GGT TGT GAT ATG CTG TGC TCG AAA       885
Cys Ser Val Ser Ala Thr Pro Leu Gly Cys Asp Met Leu Cys Ser Lys
            245                 250                 255

GCC ACG GAG ACA GAG GAA GAA GAT TAT AAC TCA GCT GTC CCT ACG CGG       933
Ala Thr Glu Thr Glu Glu Glu Asp Tyr Asn Ser Ala Val Pro Thr Arg
        260                 265                 270

ATG GTA CAT GGG AGG TTA GGG TTC GAC GGC CAA TAT CAC GAA AAG GAC       981
Met Val His Gly Arg Leu Gly Phe Asp Gly Gln Tyr His Glu Lys Asp
    275                 280                 285

CTA GAT GTC ACA ACA TTA TTC GGG GAC TGG GTG GCC AAC TAC CCA GGA      1029
Leu Asp Val Thr Thr Leu Phe Gly Asp Trp Val Ala Asn Tyr Pro Gly
290                 295                 300                 305
```

-continued

```
GTA GGG GGT GGA TCT TTT ATT GAC AGC CGC GTG TGG TTC TCA GTC TAC      1077
Val Gly Gly Gly Ser Phe Ile Asp Ser Arg Val Trp Phe Ser Val Tyr
                310                 315                 320

GGA GGG TTA AAA CCC AAT ACA CCC AGT GAC ACT GTA CAG GAA GGG AAA      1125
Gly Gly Leu Lys Pro Asn Thr Pro Ser Asp Thr Val Gln Glu Gly Lys
            325                 330                 335

TAT GTG ATA TAC AAG CGA TAC AAT GAC ACA TGC CCA GAT GAG CAA GAC      1173
Tyr Val Ile Tyr Lys Arg Tyr Asn Asp Thr Cys Pro Asp Glu Gln Asp
        340                 345                 350

TAC CAG ATT CGA ATG GCC AAG TCT TCG TAT AAG CCT GGA CGG TTT GGT      1221
Tyr Gln Ile Arg Met Ala Lys Ser Ser Tyr Lys Pro Gly Arg Phe Gly
    355                 360                 365

GGG AAA CGC ATA CAG CAG GCT ATC TTA TCT ATC AAA GTG TCA ACA TCC      1269
Gly Lys Arg Ile Gln Gln Ala Ile Leu Ser Ile Lys Val Ser Thr Ser
370                 375                 380                 385

TTA GGC GAA GAC CCG GTA CTG ACT GTA CCG CCC AAC ACA GTC ACA CTC      1317
Leu Gly Glu Asp Pro Val Leu Thr Val Pro Pro Asn Thr Val Thr Leu
                390                 395                 400

ATG GGG GCC GAA GGC AGA ATT CTC ACA GTA GGG ACA TCC CAT TTC TTG      1365
Met Gly Ala Glu Gly Arg Ile Leu Thr Val Gly Thr Ser His Phe Leu
            405                 410                 415

TAT CAG CGA GGG TCA TCA TAC TTC TCT CCC GCG TTA TTA TAT CCT ATG      1413
Tyr Gln Arg Gly Ser Ser Tyr Phe Ser Pro Ala Leu Leu Tyr Pro Met
        420                 425                 430

ACA GTC AGC AAC AAA ACA GCC ACT CTT CAT AGT CCT TAT ACA TTC AAT      1461
Thr Val Ser Asn Lys Thr Ala Thr Leu His Ser Pro Tyr Thr Phe Asn
    435                 440                 445

GCC TTC ACT CGG CCA GGT AGT ATC CCT TGC CAG GCT TCA GCA AGA TGC      1509
Ala Phe Thr Arg Pro Gly Ser Ile Pro Cys Gln Ala Ser Ala Arg Cys
450                 455                 460                 465

CCC AAC TCA TGT GTT ACT GGA GTC TAT ACA GAT CCA TAT CCC CTA ATC      1557
Pro Asn Ser Cys Val Thr Gly Val Tyr Thr Asp Pro Tyr Pro Leu Ile
                470                 475                 480

TTC TAT AGA AAC CAC ACC TTG CGA GGG GTA TTC GGG ACA ATG CTT GAT      1605
Phe Tyr Arg Asn His Thr Leu Arg Gly Val Phe Gly Thr Met Leu Asp
            485                 490                 495

GGT GAA CAA GCA AGA CTT AAC CCT GCG TCT GCA GTA TTC GAT AGC ACA      1653
Gly Glu Gln Ala Arg Leu Asn Pro Ala Ser Ala Val Phe Asp Ser Thr
        500                 505                 510

TCC CGC AGT CGC ATA ACT CGA GTG AGT TCA AGC AGC ATC AAA GCA GCA      1701
Ser Arg Ser Arg Ile Thr Arg Val Ser Ser Ser Ser Ile Lys Ala Ala
    515                 520                 525

TAC ACA ACA TCA ACT TGT TTT AAA GTG GTC AAG ACC AAT AAG ACC TAT      1749
Tyr Thr Thr Ser Thr Cys Phe Lys Val Val Lys Thr Asn Lys Thr Tyr
530                 535                 540                 545

TGT CTC AGC ATT GCT GAA ATA TCT AAT ACT CTC TTC GGA GAA TTC AGA      1797
Cys Leu Ser Ile Ala Glu Ile Ser Asn Thr Leu Phe Gly Glu Phe Arg
                550                 555                 560

ATC GTC CCG TTA CTA GTT GAG ATC CTC AAA GAT GAC GGG GTT AGA GAA      1845
Ile Val Pro Leu Leu Val Glu Ile Leu Lys Asp Asp Gly Val Arg Glu
            565                 570                 575

GCC AGG TCT GGC TAGTTGAGTC AACTATGAAA GAGTTGGAAA GATGGCATTG          1897
Ala Arg Ser Gly
        580

TATCACCTAT CTTCTGCGAC ATCAAGAATC AAACCGAATG CCCGGATCCA TAATTAATTA   1957

ATTAATTTTT ATCCCTCGAC TCTAGAAAAA ATTGAAAAAC TATTCTAATT TATTGCACGG   2017

AGATCTTTTT TTTTTTTTTT TTTTTTGGCA TATAAATGAA TTCGGATCGA TCCCGGTTGG   2077

CGCCCTCCAG GTGCAGG ATG GGC TCC AGA CCT TCT ACC AAG AAC CCA GCA      2127
```

-continued

```
                  Met Gly Ser Arg Pro Ser Thr Lys Asn Pro Ala
                    1               5                  10

CCT ATG ATG CTG ACT ATC CGG GTC GCG CTG GTA CTG AGT TGC ATC TGT     2175
Pro Met Met Leu Thr Ile Arg Val Ala Leu Val Leu Ser Cys Ile Cys
             15                  20                  25

CCG GCA AAC TCC ATT GAT GGC AGG CCT CTT GCA GCT GCA GGA ATT GTG     2223
Pro Ala Asn Ser Ile Asp Gly Arg Pro Leu Ala Ala Ala Gly Ile Val
         30                  35                  40

GTT ACA GGA GAC AAA GCA GTC AAC ATA TAC ACC TCA TCC CAG ACA GGA     2271
Val Thr Gly Asp Lys Ala Val Asn Ile Tyr Thr Ser Ser Gln Thr Gly
     45                  50                  55

TCA ATC ATA GTT AAG CTC CTC CCG AAT CTG CCA AAG GAT AAG GAG GCA     2319
Ser Ile Ile Val Lys Leu Leu Pro Asn Leu Pro Lys Asp Lys Glu Ala
 60                  65                  70                  75

TGT GCG AAA GCC CCC TTG GAT GCA TAC AAC AGG ACA TTG ACC ACT TTG     2367
Cys Ala Lys Ala Pro Leu Asp Ala Tyr Asn Arg Thr Leu Thr Thr Leu
                 80                  85                  90

CTC ACC CCC CTT GGT GAC TCT ATC CGT AGG ATA CAA GAG TCT GTG ACT     2415
Leu Thr Pro Leu Gly Asp Ser Ile Arg Arg Ile Gln Glu Ser Val Thr
             95                 100                 105

ACA TCT GGA GGG GGG AGA CAG GGG CGC CTT ATA GGC GCC ATT ATT GGC     2463
Thr Ser Gly Gly Gly Arg Gln Gly Arg Leu Ile Gly Ala Ile Ile Gly
        110                 115                 120

GGT GTG GCT CTT GGG GTT GCA ACT GCC GCA CAA ATA ACA GCG GCC GCA     2511
Gly Val Ala Leu Gly Val Ala Thr Ala Ala Gln Ile Thr Ala Ala Ala
    125                 130                 135

GCT CTG ATA CAA GCC AAA CAA AAT GCT GCC AAC ATC CTC CGA CTT AAA     2559
Ala Leu Ile Gln Ala Lys Gln Asn Ala Ala Asn Ile Leu Arg Leu Lys
140                 145                 150                 155

GAG AGC ATT GCC GCA ACC AAT GAG GCT GTG CAT GAG GTC ACT GAC GGA     2607
Glu Ser Ile Ala Ala Thr Asn Glu Ala Val His Glu Val Thr Asp Gly
                160                 165                 170

TTA TCG CAA CTA GCA GTG GCA GTT GGG AAG ATG CAG CAG TTC GTT AAT     2655
Leu Ser Gln Leu Ala Val Ala Val Gly Lys Met Gln Gln Phe Val Asn
            175                 180                 185

GAC CAA TTT AAT AAA ACA GCT CAG GAA TTA GAC TGC ATC AAA ATT GCA     2703
Asp Gln Phe Asn Lys Thr Ala Gln Glu Leu Asp Cys Ile Lys Ile Ala
        190                 195                 200

CAG CAA GTT GGT GTA GAG CTC AAC CTG TAC CTA ACC GAA TCG ACT ACA     2751
Gln Gln Val Gly Val Glu Leu Asn Leu Tyr Leu Thr Glu Ser Thr Thr
    205                 210                 215

GTA TTC GGA CCA CAA ATC ACT TCA CCT GCC TTA AAC AAG CTG ACT ATT     2799
Val Phe Gly Pro Gln Ile Thr Ser Pro Ala Leu Asn Lys Leu Thr Ile
220                 225                 230                 235

CAG GCA CTT TAC AAT CTA GCT GGT GGG AAT ATG GAT TAC TTA TTG ACT     2847
Gln Ala Leu Tyr Asn Leu Ala Gly Gly Asn Met Asp Tyr Leu Leu Thr
                240                 245                 250

AAG TTA GGT ATA GGG AAC AAT CAA CTC AGC TCA TTA ATC GGT AGC GGC     2895
Lys Leu Gly Ile Gly Asn Asn Gln Leu Ser Ser Leu Ile Gly Ser Gly
            255                 260                 265

TTA ATC ACC GGT AAC CCT ATT CTA TAC GAC TCA CAG ACT CAA CTC TTG     2943
Leu Ile Thr Gly Asn Pro Ile Leu Tyr Asp Ser Gln Thr Gln Leu Leu
        270                 275                 280

GGT ATA CAG GTA ACT CTA CCT TCA GTC GGG AAC CTA AAT AAT ATG CGT     2991
Gly Ile Gln Val Thr Leu Pro Ser Val Gly Asn Leu Asn Asn Met Arg
    285                 290                 295

GCC ACC TAC TTG GAA ACC TTA TCC GTA AGC ACA ACC AGG GGA TTT GCC     3039
Ala Thr Tyr Leu Glu Thr Leu Ser Val Ser Thr Thr Arg Gly Phe Ala
300                 305                 310                 315
```

-continued

```
TCG GCA CTT GTC CCA AAA GTG GTG ACA CGG GTC GGT TCT GTG ATA GAA     3087
Ser Ala Leu Val Pro Lys Val Val Thr Arg Val Gly Ser Val Ile Glu
            320                 325                 330

GAA CTT GAC ACC TCA TAC TGT ATA GAA ACT GAC TTA GAT TTA TAT TGT     3135
Glu Leu Asp Thr Ser Tyr Cys Ile Glu Thr Asp Leu Asp Leu Tyr Cys
            335                 340                 345

ACA AGA ATA GTA ACG TTC CCT ATG TCC CCT GGT ATT TAC TCC TGC TTG     3183
Thr Arg Ile Val Thr Phe Pro Met Ser Pro Gly Ile Tyr Ser Cys Leu
        350                 355                 360

AGC GGC AAT ACA TCG GCC TGT ATG TAC TCA AAG ACC GAA GGC GCA CTT     3231
Ser Gly Asn Thr Ser Ala Cys Met Tyr Ser Lys Thr Glu Gly Ala Leu
    365                 370                 375

ACT ACA CCA TAT ATG ACT ATC AAA GGC TCA GTC ATC GCT AAC TGC AAG     3279
Thr Thr Pro Tyr Met Thr Ile Lys Gly Ser Val Ile Ala Asn Cys Lys
380                 385                 390                 395

ATG ACA ACA TGT AGA TGT GTA AAC CCC CCG GGT ATC ATA TCG CAA AAC     3327
Met Thr Thr Cys Arg Cys Val Asn Pro Pro Gly Ile Ile Ser Gln Asn
            400                 405                 410

TAT GGA GAA GCC GTG TCT CTA ATA GAT AAA CAA TCA TGC AAT GTT TTA     3375
Tyr Gly Glu Ala Val Ser Leu Ile Asp Lys Gln Ser Cys Asn Val Leu
            415                 420                 425

TCC TTA GGC GGG ATA ACT TTA AGG CTC AGT GGG GAA TTC GAT GTA ACT     3423
Ser Leu Gly Gly Ile Thr Leu Arg Leu Ser Gly Glu Phe Asp Val Thr
        430                 435                 440

TAT CAG AAG AAT ATC TCA ATA CAA GAT TCT CAA GTA ATA ATA ACA GGC     3471
Tyr Gln Lys Asn Ile Ser Ile Gln Asp Ser Gln Val Ile Ile Thr Gly
    445                 450                 455

AAT CTT GAT ATC TCA ACT GAG CTT GGG AAT GTC AAC AAC TCG ATC AGT     3519
Asn Leu Asp Ile Ser Thr Glu Leu Gly Asn Val Asn Asn Ser Ile Ser
460                 465                 470                 475

AAT GCC TTG AAT AAG TTA GAG GAA AGC AAC AGA AAA CTA GAC AAA GTC     3567
Asn Ala Leu Asn Lys Leu Glu Glu Ser Asn Arg Lys Leu Asp Lys Val
            480                 485                 490

AAT GTC AAA CTG ACC AGC ACA TCT GCT CTC ATT ACC TAT ATC GTT TTG     3615
Asn Val Lys Leu Thr Ser Thr Ser Ala Leu Ile Thr Tyr Ile Val Leu
            495                 500                 505

ACT ATC ATA TCT CTT GTT TTT GGT ATA CTT AGC CTG ATT CTA GCA TGC     3663
Thr Ile Ile Ser Leu Val Phe Gly Ile Leu Ser Leu Ile Leu Ala Cys
        510                 515                 520

TAC CTA ATG TAC AAG CAA AAG GCG CAA CAA AAG ACC TTA TTA TGG CTT     3711
Tyr Leu Met Tyr Lys Gln Lys Ala Gln Gln Lys Thr Leu Leu Trp Leu
    525                 530                 535

GGG AAT AAT ACC CTA GAT CAG ATG AGA GCC ACT ACA AAA ATG TGAACACAGA  3763
Gly Asn Asn Thr Leu Asp Gln Met Arg Ala Thr Thr Lys Met
540                 545                 550

TGAGGAACGA AGGTTTCCCT AATAGTAATT TGTGTGAAAG TTCTGGTAGT CTGTCAGTTC   3823

GGAGAGTTAA GAAAAAAAAA AAACCCCCCC CCCCCCCCCC CCCCCCCCCT GCAGGCATCG   3883

TGGTGTCACG CTCGTCGTTT GGTATGGCTT CATTCAGCTC CGGTTCCCAA CGATCAAGGC   3943

GAGTTACATG ATCCCCCATG TTGTGCAAAA AAGCGGTTAG CTCCTTCGGT CCTCCGATCG   4003

TTGTCAGAAG TAAGTTGGCC GCAGTGTTAT CACTCATGGT TATGGCAGCA CTGCATAATT   4063

CTCTTACTGT CATGCCATCC GTAAGATGCT TTTCTGTGAC TGGTGAGTGA TCCATAATTA   4123

ATTAATTAAT TTTTATCCCG GGTCGACCTG CAGGCGGCCG CGGCCCTCGA GGCC         4177
```

(2) INFORMATION FOR SEQ ID NO:13:

(i) SEQUENCE CHARACTERISTICS:
(A) LENGTH: 581 amino acids

-continued (B) TYPE: amino acid
(D) TOPOLOGY: linear (ii) MOLECULE TYPE: protein (xi) SEQUENCE DESCRIPTION: SEQ ID NO:13:

```
Met Asn Ser Asp Pro Asp Arg Ala Val Ser Gln Val Ala Leu Glu Asn
  1               5                  10                  15

Asp Glu Arg Glu Ala Lys Asn Thr Trp Arg Leu Ile Phe Arg Ile Ala
             20                  25                  30

Ile Leu Phe Leu Thr Val Val Thr Leu Ala Ile Ser Val Ala Ser Leu
         35                  40                  45

Leu Tyr Ser Met Gly Ala Ser Thr Pro Ser Asp Leu Val Gly Ile Pro
     50                  55                  60

Thr Arg Ile Ser Arg Ala Glu Glu Lys Ile Thr Ser Thr Leu Gly Ser
 65                  70                  75                  80

Asn Gln Asp Val Val Asp Arg Ile Tyr Lys Gln Val Ala Leu Glu Ser
                 85                  90                  95

Pro Leu Ala Leu Leu Asn Thr Glu Thr Thr Ile Met Asn Ala Ile Thr
            100                 105                 110

Ser Leu Ser Tyr Gln Ile Asn Gly Ala Ala Asn Asn Ser Gly Trp Gly
        115                 120                 125

Ala Pro Ile His Asp Pro Asp Tyr Ile Gly Gly Ile Gly Lys Glu Leu
    130                 135                 140

Ile Val Asp Asp Ala Ser Asp Val Thr Ser Phe Tyr Pro Ser Ala Phe
145                 150                 155                 160

Gln Glu His Leu Asn Phe Ile Pro Ala Pro Thr Thr Gly Ser Gly Cys
                165                 170                 175

Thr Arg Ile Pro Ser Phe Asp Met Ser Ala Thr His Tyr Cys Tyr Thr
            180                 185                 190

His Asn Val Ile Leu Ser Gly Cys Arg Asp His Ser His Ser His Gln
        195                 200                 205

Tyr Leu Ala Leu Gly Val Leu Arg Thr Ser Ala Thr Gly Arg Val Phe
    210                 215                 220

Phe Ser Thr Leu Arg Ser Ile Asn Leu Asp Asp Thr Gln Asn Arg Lys
225                 230                 235                 240

Ser Cys Ser Val Ser Ala Thr Pro Leu Gly Cys Asp Met Leu Cys Ser
                245                 250                 255

Lys Ala Thr Glu Thr Glu Glu Glu Asp Tyr Asn Ser Ala Val Pro Thr
            260                 265                 270

Arg Met Val His Gly Arg Leu Gly Phe Asp Gly Gln Tyr His Glu Lys
        275                 280                 285

Asp Leu Asp Val Thr Thr Leu Phe Gly Asp Trp Val Ala Asn Tyr Pro
    290                 295                 300

Gly Val Gly Gly Gly Ser Phe Ile Asp Ser Arg Val Trp Phe Ser Val
305                 310                 315                 320

Tyr Gly Gly Leu Lys Pro Asn Thr Pro Ser Asp Thr Val Gln Glu Gly
                325                 330                 335

Lys Tyr Val Ile Tyr Lys Arg Tyr Asn Asp Thr Cys Pro Asp Glu Gln
            340                 345                 350

Asp Tyr Gln Ile Arg Met Ala Lys Ser Ser Tyr Lys Pro Gly Arg Phe
        355                 360                 365

Gly Gly Lys Arg Ile Gln Gln Ala Ile Leu Ser Ile Lys Val Ser Thr
    370                 375                 380
```

-continued

```
Ser Leu Gly Glu Asp Pro Val Leu Thr Val Pro Pro Asn Thr Val Thr
385                 390                 395                 400

Leu Met Gly Ala Glu Gly Arg Ile Leu Thr Val Gly Thr Ser His Phe
                405                 410                 415

Leu Tyr Gln Arg Gly Ser Ser Tyr Phe Ser Pro Ala Leu Leu Tyr Pro
            420                 425                 430

Met Thr Val Ser Asn Lys Thr Ala Thr Leu His Ser Pro Tyr Thr Phe
        435                 440                 445

Asn Ala Phe Thr Arg Pro Gly Ser Ile Pro Cys Gln Ala Ser Ala Arg
    450                 455                 460

Cys Pro Asn Ser Cys Val Thr Gly Val Tyr Thr Asp Pro Tyr Pro Leu
465                 470                 475                 480

Ile Phe Tyr Arg Asn His Thr Leu Arg Gly Val Phe Gly Thr Met Leu
                485                 490                 495

Asp Gly Glu Gln Ala Arg Leu Asn Pro Ala Ser Ala Val Phe Asp Ser
            500                 505                 510

Thr Ser Arg Ser Arg Ile Thr Arg Val Ser Ser Ser Ser Ile Lys Ala
        515                 520                 525

Ala Tyr Thr Thr Ser Thr Cys Phe Lys Val Val Lys Thr Asn Lys Thr
    530                 535                 540

Tyr Cys Leu Ser Ile Ala Glu Ile Ser Asn Thr Leu Phe Gly Glu Phe
545                 550                 555                 560

Arg Ile Val Pro Leu Leu Val Glu Ile Leu Lys Asp Asp Gly Val Arg
                565                 570                 575

Glu Ala Arg Ser Gly
            580
```

(2) INFORMATION FOR SEQ ID NO:14:

(i) SEQUENCE CHARACTERISTICS:
(A) LENGTH: 553 amino acids
(B) TYPE: amino acid
(D) TOPOLOGY: linear (ii) MOLECULE TYPE: protein (xi) SEQUENCE DESCRIPTION: SEQ ID NO:14:

```
Met Gly Ser Arg Pro Ser Thr Lys Asn Pro Ala Pro Met Met Leu Thr
  1               5                  10                  15

Ile Arg Val Ala Leu Val Leu Ser Cys Ile Cys Pro Ala Asn Ser Ile
             20                  25                  30

Asp Gly Arg Pro Leu Ala Ala Ala Gly Ile Val Val Thr Gly Asp Lys
         35                  40                  45

Ala Val Asn Ile Tyr Thr Ser Ser Gln Thr Gly Ser Ile Ile Val Lys
     50                  55                  60

Leu Leu Pro Asn Leu Pro Lys Asp Lys Glu Ala Cys Ala Lys Ala Pro
 65                  70                  75                  80

Leu Asp Ala Tyr Asn Arg Thr Leu Thr Thr Leu Leu Thr Pro Leu Gly
                 85                  90                  95

Asp Ser Ile Arg Arg Ile Gln Glu Ser Val Thr Thr Ser Gly Gly Gly
            100                 105                 110

Arg Gln Gly Arg Leu Ile Gly Ala Ile Ile Gly Gly Val Ala Leu Gly
        115                 120                 125

Val Ala Thr Ala Ala Gln Ile Thr Ala Ala Ala Ala Leu Ile Gln Ala
    130                 135                 140

Lys Gln Asn Ala Ala Asn Ile Leu Arg Leu Lys Glu Ser Ile Ala Ala
```

-continued

```
145                 150                 155                 160

Thr Asn Glu Ala Val His Glu Val Thr Asp Gly Leu Ser Gln Leu Ala
                165                 170                 175

Val Ala Val Gly Lys Met Gln Gln Phe Val Asn Asp Gln Phe Asn Lys
            180                 185                 190

Thr Ala Gln Glu Leu Asp Cys Ile Lys Ile Ala Gln Gln Val Gly Val
        195                 200                 205

Glu Leu Asn Leu Tyr Leu Thr Glu Ser Thr Thr Val Phe Gly Pro Gln
    210                 215                 220

Ile Thr Ser Pro Ala Leu Asn Lys Leu Thr Ile Gln Ala Leu Tyr Asn
225                 230                 235                 240

Leu Ala Gly Gly Asn Met Asp Tyr Leu Leu Thr Lys Leu Gly Ile Gly
                245                 250                 255

Asn Asn Gln Leu Ser Ser Leu Ile Gly Ser Gly Leu Ile Thr Gly Asn
            260                 265                 270

Pro Ile Leu Tyr Asp Ser Gln Thr Gln Leu Leu Gly Ile Gln Val Thr
        275                 280                 285

Leu Pro Ser Val Gly Asn Leu Asn Asn Met Arg Ala Thr Tyr Leu Glu
    290                 295                 300

Thr Leu Ser Val Ser Thr Thr Arg Gly Phe Ala Ser Ala Leu Val Pro
305                 310                 315                 320

Lys Val Val Thr Arg Val Gly Ser Val Ile Glu Glu Leu Asp Thr Ser
                325                 330                 335

Tyr Cys Ile Glu Thr Asp Leu Asp Leu Tyr Cys Thr Arg Ile Val Thr
            340                 345                 350

Phe Pro Met Ser Pro Gly Ile Tyr Ser Cys Leu Ser Gly Asn Thr Ser
        355                 360                 365

Ala Cys Met Tyr Ser Lys Thr Glu Gly Ala Leu Thr Thr Pro Tyr Met
    370                 375                 380

Thr Ile Lys Gly Ser Val Ile Ala Asn Cys Lys Met Thr Thr Cys Arg
385                 390                 395                 400

Cys Val Asn Pro Pro Gly Ile Ile Ser Gln Asn Tyr Gly Glu Ala Val
                405                 410                 415

Ser Leu Ile Asp Lys Gln Ser Cys Asn Val Leu Ser Leu Gly Gly Ile
            420                 425                 430

Thr Leu Arg Leu Ser Gly Glu Phe Asp Val Thr Tyr Gln Lys Asn Ile
        435                 440                 445

Ser Ile Gln Asp Ser Gln Val Ile Ile Thr Gly Asn Leu Asp Ile Ser
    450                 455                 460

Thr Glu Leu Gly Asn Val Asn Asn Ser Ile Ser Asn Ala Leu Asn Lys
465                 470                 475                 480

Leu Glu Glu Ser Asn Arg Lys Leu Asp Lys Val Asn Val Lys Leu Thr
                485                 490                 495

Ser Thr Ser Ala Leu Ile Thr Tyr Ile Val Leu Thr Ile Ile Ser Leu
            500                 505                 510

Val Phe Gly Ile Leu Ser Leu Ile Leu Ala Cys Tyr Leu Met Tyr Lys
        515                 520                 525

Gln Lys Ala Gln Gln Lys Thr Leu Leu Trp Leu Gly Asn Asn Thr Leu
    530                 535                 540

Asp Gln Met Arg Ala Thr Thr Lys Met
545                 550
```

(2) INFORMATION FOR SEQ ID NO:15:

-continued (i) SEQUENCE CHARACTERISTICS:
(A) LENGTH: 182 base pairs
(B) TYPE: nucleic acid
(C) STRANDEDNESS: double
(D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:15:

GGCCTCGAGG GCCGCGGCCG CCTGCAGGTC GACTCTAGAA AAAATTGAAA AACTATTCTA 60

ATTTATTGCA CGGAGATCTT TTTTTTTTTT TTTTTTTTTG GCATATAAAT GAATTCGGAT 120

CCGGACCGCG CCGTTAGCCA AGTTGCGTTA GAGAATGATG AAAGAGAGGC AAAAAATACA 180

TG 182

(2) INFORMATION FOR SEQ ID NO:16:

(i) SEQUENCE CHARACTERISTICS:
(A) LENGTH: 178 base pairs
(B) TYPE: nucleic acid
(C) STRANDEDNESS: double
(D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:16:

ATCTTCTGCG ACATCAAGAA TCAAACCGAA TGCCCGGATC CATAATTAAT TAATTAATTT 60

TTATCCCTCG ACTCTAGAAA AAATTGAAAA ACTATTCTAA TTTATTGCAC GGAGATCTTT 120

TTTTTTTTTT TTTTTTTTGG CATATAAATG AATTCGGATC GATCCCGGTT GGCGCCCT 178

(2) INFORMATION FOR SEQ ID NO:17:

(i) SEQUENCE CHARACTERISTICS:
(A) LENGTH: 60 base pairs
(B) TYPE: nucleic acid
(C) STRANDEDNESS: double
(D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:17:

AAAAACCCCC CCCCCCCCCC CCCCCCCCCC CTGCAGGCAT CGTGGTGTCA CGCTCGTCGT 60

(2) INFORMATION FOR SEQ ID NO:18:

(i) SEQUENCE CHARACTERISTICS:
(A) LENGTH: 120 base pairs
(B) TYPE: nucleic acid
(C) STRANDEDNESS: double
(D) TOPOLOGY: linear (ii) MOLECULE TYPE: DNA (genomic)

(iii) HYPOTHETICAL: NO (iv) ANTI-SENSE: NO

-continued (xi) SEQUENCE DESCRIPTION: SEQ ID NO:18:

```
ATAATTCTCT TACTGTCATG CCATCCGTAA GATGCTTTTC TGTGACTGGT GAGTGATCCA     60

TAATTAATTA ATTAATTTTT ATCCCGGGTC GACCTGCAGG CGGCCGCGGC CCTCGAGGCC    120
```

(2) INFORMATION FOR SEQ ID NO:19:

(i) SEQUENCE CHARACTERISTICS:
(A) LENGTH: 1305 base pairs
(B) TYPE: nucleic acid
(C) STRANDEDNESS: double
(D) TOPOLOGY: linear (ii) MOLECULE TYPE: DNA (genomic)

(iii) HYPOTHETICAL: NO (iv) ANTI-SENSE: NO (ix) FEATURE:
(A) NAME/KEY: CDS
(B) LOCATION: 1..1305

(xi) SEQUENCE DESCRIPTION: SEQ ID NO:19:

```
ATG CAC CGT CCT CAT CTC AGA CGG CAC TCG CGT TAC TAC GCG AAA GGA       48
Met His Arg Pro His Leu Arg Arg His Ser Arg Tyr Tyr Ala Lys Gly
  1               5                  10                  15

GAG GTG CTT AAC AAA CAC ATG GAT TGC GGT GGA AAA CGG TGC TGC TCA       96
Glu Val Leu Asn Lys His Met Asp Cys Gly Gly Lys Arg Cys Cys Ser
             20                  25                  30

GGC GCA GCT GTA TTC ACT CTT TTC TGG ACT TGT GTC AGG ATT ATG CGG      144
Gly Ala Ala Val Phe Thr Leu Phe Trp Thr Cys Val Arg Ile Met Arg
         35                  40                  45

GAG CAT ATC TGC TTT GTA CGC AAC GCT ATG GAC CGC CAT TTA TTT TTG      192
Glu His Ile Cys Phe Val Arg Asn Ala Met Asp Arg His Leu Phe Leu
     50                  55                  60

AGG AAT GCT TTT TGG ACT ATC GTA CTG CTT TCT TCC TTC GCT AGC CAG      240
Arg Asn Ala Phe Trp Thr Ile Val Leu Leu Ser Ser Phe Ala Ser Gln
 65                  70                  75                  80

AGC ACC GCC GCC GTC ACG TAC GAC TAC ATT TTA GGC CGT CGC GCG CTC      288
Ser Thr Ala Ala Val Thr Tyr Asp Tyr Ile Leu Gly Arg Arg Ala Leu
                 85                  90                  95

GAC GCG CTA ACC ATA CCG GCG GTT GGC CCG TAT AAC AGA TAC CTC ACT      336
Asp Ala Leu Thr Ile Pro Ala Val Gly Pro Tyr Asn Arg Tyr Leu Thr
            100                 105                 110

AGG GTA TCA AGA GGC TGC GAC GTT GTC GAG CTC AAC CCG ATT TCT AAC      384
Arg Val Ser Arg Gly Cys Asp Val Val Glu Leu Asn Pro Ile Ser Asn
        115                 120                 125

GTG GAC GAC ATG ATA TCG GCG GCC AAA GAA AAA GAG AAG GGG GGC CCT      432
Val Asp Asp Met Ile Ser Ala Ala Lys Glu Lys Glu Lys Gly Gly Pro
    130                 135                 140

TTC GAG GCC TCC GTC GTC TGG TTC TAC GTG ATT AAG GGC GAC GAC GGC      480
Phe Glu Ala Ser Val Val Trp Phe Tyr Val Ile Lys Gly Asp Asp Gly
145                 150                 155                 160

GAG GAC AAG TAC TGT CCA ATC TAT AGA AAA GAG TAC AGG GAA TGT GGC      528
Glu Asp Lys Tyr Cys Pro Ile Tyr Arg Lys Glu Tyr Arg Glu Cys Gly
                165                 170                 175

GAC GTA CAA CTG CTA TCT GAA TGC GCC GTT CAA TCT GCA CAG ATG TGG      576
Asp Val Gln Leu Leu Ser Glu Cys Ala Val Gln Ser Ala Gln Met Trp
            180                 185                 190

GCA GTG GAC TAT GTT CCT AGC ACC CTT GTA TCG CGA AAT GGC GCG GGA      624
Ala Val Asp Tyr Val Pro Ser Thr Leu Val Ser Arg Asn Gly Ala Gly
        195                 200                 205
```

-continued

```
CTG ACT ATA TTC TCC CCC ACT GCT GCG CTC TCT GGC CAA TAC TTG CTG      672
Leu Thr Ile Phe Ser Pro Thr Ala Ala Leu Ser Gly Gln Tyr Leu Leu
    210                 215                 220

ACC CTG AAA ATC GGG AGA TTT GCG CAA ACA GCT CTC GTA ACT CTA GAA      720
Thr Leu Lys Ile Gly Arg Phe Ala Gln Thr Ala Leu Val Thr Leu Glu
225                 230                 235                 240

GTT AAC GAT CGC TGT TTA AAG ATC GGG TCG CAG CTT AAC TTT TTA CCG      768
Val Asn Asp Arg Cys Leu Lys Ile Gly Ser Gln Leu Asn Phe Leu Pro
                245                 250                 255

TCG AAA TGC TGG ACA ACA GAA CAG TAT CAG ACT GGA TTT CAA GGC GAA      816
Ser Lys Cys Trp Thr Thr Glu Gln Tyr Gln Thr Gly Phe Gln Gly Glu
            260                 265                 270

CAC CTT TAT CCG ATC GCA GAC ACC AAT ACA CGA CAC GCG GAC GAC GTA      864
His Leu Tyr Pro Ile Ala Asp Thr Asn Thr Arg His Ala Asp Asp Val
        275                 280                 285

TAT CGG GGA TAC GAA GAT ATT CTG CAG CGC TGG AAT AAT TTG CTG AGG      912
Tyr Arg Gly Tyr Glu Asp Ile Leu Gln Arg Trp Asn Asn Leu Leu Arg
    290                 295                 300

AAA AAG AAT CCT AGC GCG CCA GAC CCT CGT CCA GAT AGC GTC CCG CAA      960
Lys Lys Asn Pro Ser Ala Pro Asp Pro Arg Pro Asp Ser Val Pro Gln
305                 310                 315                 320

GAA ATT CCC GCT GTA ACC AAG AAA GCG GAA GGG CGC ACC CCG GAC GCA     1008
Glu Ile Pro Ala Val Thr Lys Lys Ala Glu Gly Arg Thr Pro Asp Ala
                325                 330                 335

GAA AGC AGC GAA AAG AAG GCC CCT CCA GAA GAC TCG GAG GAC GAC ATG     1056
Glu Ser Ser Glu Lys Lys Ala Pro Pro Glu Asp Ser Glu Asp Asp Met
            340                 345                 350

CAG GCA GAG GCT TCT GGA GAA AAT CCT GCC GCC CTC CCC GAA GAC GAC     1104
Gln Ala Glu Ala Ser Gly Glu Asn Pro Ala Ala Leu Pro Glu Asp Asp
        355                 360                 365

GAA GTC CCC GAG GAC ACC GAG CAC GAT GAT CCA AAC TCG GAT CCT GAC     1152
Glu Val Pro Glu Asp Thr Glu His Asp Asp Pro Asn Ser Asp Pro Asp
    370                 375                 380

TAT TAC AAT GAC ATG CCC GCC GTG ATC CCG GTG GAG GAG ACT ACT AAA     1200
Tyr Tyr Asn Asp Met Pro Ala Val Ile Pro Val Glu Glu Thr Thr Lys
385                 390                 395                 400

AGT TCT AAT GCC GTC TCC ATG CCC ATA TTC GCG GCG TTC GTA GCC TGC     1248
Ser Ser Asn Ala Val Ser Met Pro Ile Phe Ala Ala Phe Val Ala Cys
                405                 410                 415

GCG GTC GCG CTC GTG GGG CTA CTG GTT TGG AGC ATC GTA AAA TGC GCG     1296
Ala Val Ala Leu Val Gly Leu Leu Val Trp Ser Ile Val Lys Cys Ala
            420                 425                 430

CGT AGC TAA                                                         1305
Arg Ser
        435
```

(2) INFORMATION FOR SEQ ID NO:20:

(i) SEQUENCE CHARACTERISTICS:
(A) LENGTH: 434 amino acids
(B) TYPE: amino acid
(D) TOPOLOGY: linear (ii) MOLECULE TYPE: protein (xi) SEQUENCE DESCRIPTION: SEQ ID NO:20:

```
Met His Arg Pro His Leu Arg Arg His Ser Arg Tyr Tyr Ala Lys Gly
  1               5                  10                  15

Glu Val Leu Asn Lys His Met Asp Cys Gly Gly Lys Arg Cys Cys Ser
             20                  25                  30
```

-continued

```
Gly Ala Ala Val Phe Thr Leu Phe Trp Thr Cys Val Arg Ile Met Arg
        35                  40                  45

Glu His Ile Cys Phe Val Arg Asn Ala Met Asp Arg His Leu Phe Leu
    50                  55                  60

Arg Asn Ala Phe Trp Thr Ile Val Leu Leu Ser Ser Phe Ala Ser Gln
 65                  70                  75                  80

Ser Thr Ala Ala Val Thr Tyr Asp Tyr Ile Leu Gly Arg Arg Ala Leu
                85                  90                  95

Asp Ala Leu Thr Ile Pro Ala Val Gly Pro Tyr Asn Arg Tyr Leu Thr
            100                 105                 110

Arg Val Ser Arg Gly Cys Asp Val Val Glu Leu Asn Pro Ile Ser Asn
        115                 120                 125

Val Asp Asp Met Ile Ser Ala Ala Lys Glu Lys Glu Lys Gly Gly Pro
    130                 135                 140

Phe Glu Ala Ser Val Val Trp Phe Tyr Val Ile Lys Gly Asp Asp Gly
145                 150                 155                 160

Glu Asp Lys Tyr Cys Pro Ile Tyr Arg Lys Glu Tyr Arg Glu Cys Gly
                165                 170                 175

Asp Val Gln Leu Leu Ser Glu Cys Ala Val Gln Ser Ala Gln Met Trp
            180                 185                 190

Ala Val Asp Tyr Val Pro Ser Thr Leu Val Ser Arg Asn Gly Ala Gly
        195                 200                 205

Leu Thr Ile Phe Ser Pro Thr Ala Ala Leu Ser Gly Gln Tyr Leu Leu
    210                 215                 220

Thr Leu Lys Ile Gly Arg Phe Ala Gln Thr Ala Leu Val Thr Leu Glu
225                 230                 235                 240

Val Asn Asp Arg Cys Leu Lys Ile Gly Ser Gln Leu Asn Phe Leu Pro
                245                 250                 255

Ser Lys Cys Trp Thr Thr Glu Gln Tyr Gln Thr Gly Phe Gln Gly Glu
            260                 265                 270

His Leu Tyr Pro Ile Ala Asp Thr Asn Thr Arg His Ala Asp Asp Val
        275                 280                 285

Tyr Arg Gly Tyr Glu Asp Ile Leu Gln Arg Trp Asn Asn Leu Leu Arg
    290                 295                 300

Lys Lys Asn Pro Ser Ala Pro Asp Pro Arg Pro Asp Ser Val Pro Gln
305                 310                 315                 320

Glu Ile Pro Ala Val Thr Lys Lys Ala Glu Gly Arg Thr Pro Asp Ala
                325                 330                 335

Glu Ser Ser Glu Lys Lys Ala Pro Pro Glu Asp Ser Glu Asp Asp Met
            340                 345                 350

Gln Ala Glu Ala Ser Gly Glu Asn Pro Ala Ala Leu Pro Glu Asp Asp
        355                 360                 365

Glu Val Pro Glu Asp Thr Glu His Asp Asp Pro Asn Ser Asp Pro Asp
    370                 375                 380

Tyr Tyr Asn Asp Met Pro Ala Val Ile Pro Val Glu Glu Thr Thr Lys
385                 390                 395                 400

Ser Ser Asn Ala Val Ser Met Pro Ile Phe Ala Ala Phe Val Ala Cys
                405                 410                 415

Ala Val Ala Leu Val Gly Leu Leu Val Trp Ser Ile Val Lys Cys Ala
            420                 425                 430

Arg Ser
```

RECOMBINANT FOWLPOX VIRUS S-FPV-043 AND USES THEREOF

This application is a continuation of U.S. Ser. No. 08/024,156, filed Feb. 26, 1993.

FIELD OF THE INVENTION

The present invention relates to a recombinant fowlpox virus useful in a live vaccine to protect fowl against Newcastle disease virus and fowlpox virus.

BACKGROUND OF THE INVENTION

The ability to isolate DNA and clone this isolated DNA into bacterial plasmids has greatly expanded the approaches available to make viral vaccines. The method used to make the present invention involve modifying cloned DNA sequences by insertions, deletions and/or single or multiple base changes. The modified DNA is then inserted into a viral genome, and the resulting virus may then be used in a vaccine to elicit an immune response in a host animal and provide protection to the animal against disease.

Fowlpox virus (FPV) is a member of the poxviridiae family of viruses. There are two subfamilies in this classification, and they are differentiated based upon the host range (vertebrate or invertebrate) of the virus. Among the vertebrate poxviruses, there is serological cross reactivity to group specific antigens that has aided in classification of the viruses into six genera, and FPV has been placed in the avipoxvirus genera along with seven additional poxviruses that primarily infect birds. In general, poxviruses are the largest of the animal viruses and can be visualized with the light microscope. Under the electron microscope, the virus takes on a biscuit like or oval shaped appearance. The principal chemical components of the poxviruses are protein (90% by weight), deoxyribonucleic acid (DNA) (3%) and lipid (5%), but in FPV the lipid component is approximately ⅓ of the dry weight. Polyacrylamide gel electrophoresis (PAGE) of solubilized virions indicates that there are >100 different proteins associated with the viruses that include: structural polypeptides, enzymes associated with translation of messenger ribonucleic acid (mRNA), enzymes involved in RNA synthesis, and enzymes associated with DNA replication. The genome of poxviruses consists of double-stranded DNA that varies in base composition (32% G+C to 64% G+C) and length (140 kilobasepairs [kb] to 280 kb for FPV) depending upon the individual virus. The complete nucleotide sequence of the vaccina virus genome has recently been determined, and most of the essential genes have been found to lie within the highly conserved middle region of the genome while nonessential functions seem to map nearer to the termini of the DNA. The poxviruses are unique in their propensity to replicate within the cytoplasmic space of the infected cell, and in the case of VV, mature virus particles are moved out of the assembly areas and into the periphery of the cell where additional membrane encapsulation occurs. With FPV, the assembled viral particles become associated with a dense viral-derived protein matrix that occludes the virus in the form of cellular inclusions that may help protect the virion from lytic activities. Depending upon the specific poxvirus and strain (from 1% to 30% of different mature VV strains) varying levels of mature virus can be found extracellularly, but the majority of the virus population remains associated with the cell at the end of the growth cycle.

Fowlpox is unique throughout the world, but because its host-range is limited to birds it is not considered to be a public health hazard. All chickens can be infected by the virus with a resulting decline in the growth rate of the bird and temporary decreases in egg production. Usually, transmission of FPV occurs through physical contact of injured skin, but there are reports that the virus is also transmitted via arthropod vectors. After an incubation period of four to ten days, the disease is typically manifested in the following ways: skin lesions in non-feathered areas, lesions of the nasal passages, and lesions of the mouth. A normal FPV infection usually lasts three to four weeks, and afterward the bird is conferred life-long immunity to the disease.

Currently, conventionally derived FPV vaccines are being used in commercial settings to provide protection to chickens and turkeys. Typically, the vaccine viruses are attenuated by serial passage in cell culture selecting for strains that have altered growth and/or virulence properties. The modified live vaccine is prepared by growth in vitro in chicken embryo fibroblast cells or by growth on the chorioallantoic membrane of the chicken embryo. The vaccine virus is typically given to birds subcutaneously.

The present invention concerns the use of FPV as a vector for the delivery of specific vaccine antigens to poultry. The idea of using live viruses as delivery systems for antigens (vectoring) has a long history that is associated with introduction of the first live viral vaccines. The antigens that were delivered were not foreign but were naturally expressed by the live virus in the vaccine. The use of viruses to deliver foreign antigens in the modern sense became possible with the advent of recombinant DNA methods. The vaccinia virus was the first such vector and various antigens from other disease-causing pathogens were used as the foreign antigens in a vaccine was created by genetic engineering. While the concept begins with these disclosures, the answers to more practical questions concerning what makes the best candidate viral vector and what constitutes the best foreign gene or gene to be delivered were not obvious. In answering these questions, details of the pathogenicity, site of replication or growth, the kind of elicited immune response, expression levels for the virus and foreign gene of interest, its suitability for genetic engineering, its probability of being licensed by regulatory agencies, etc. needed to be addressed.

The presently preferred method for creating a recombinant poxvirus uses a plasmid of bacterial origin that contains at least one cassette consisting of a poxvirus promoter followed by the gene of interest. The cassette(s) is flanked by poxvirus genomic DNA sequences that direct insertion of the gene of interest into the corresponding homologous nonessential region of the viral genome by homologous recombination. Cells are initially infected with the wild-type virus, and shortly thereafter the plasmid DNA is introduced into the infected cells. Since poxviruses have their own RNA polymerase and transcriptional apparatus, it is necessary that the gene of interest be regulated by a promoter of poxvirus origin. There are three characteristic poxvirus promoters that are differentiated based upon their temporal regulation of gene expression relative to the infective cycle of the virus: early, intermediate and late expression. Each promoter type can be identified by a typical consensus sequence that is approximately 30 bp in length and specific to each promoter type. In vaccinia virus, some viral genes are regulated by tandem early/late promoters that can be used by the virus to continually express the downstream gene throughout the infective cycle.

It is generally agreed that poxviruses contain nonessential regions of DNA in various parts of the genome, and that modifications of these regions can either attenuate the virus, leading to a non-pathogenic strain from which a vaccine may be derived, or give rise to genomic instabilities that yield mixed populations of virus. The degree of attenuation of the virus is important to the utility of the virus as a vaccine. Insertions or deletions which cause too much attenuation or genetic deletions which cause too much attenuation or genetic instability of the virus will result in a vaccine that fails to elicit an adequate immune response. Although several examples of deletions/insertions are known for poxviruses, the appropriate configuration is not readily apparent.

Thus far, gene expression from foreign genes of interest inserted into the genome of poxviruses has been obtained for five different pox viruses: vaccinia, canary pox, pigeon pox, raccoon pox and fowlpox. Vaccinia virus is the classically studied poxvirus, and it has been used extensively to vector foreign genes of interest (see U.S. Pat. Nos. 4,603,112 (1986) and 4,722,848 (1988). Raccoon pox (Esposito, et al., 1988) and Canary pox (Taylor, et al., 1991) have bene used to express antigens from the rabies virus. More recently, FPV has been used to vector a number of different foreign genes of interest, and is the subject of several published patent applications (EPA 0 284 416 (1988), PCT WO 89/03429 (1989), PCT WO 89/12684 (1989), PCT WO 91/02072 (1991), PCT WO 89/03879 (1989)). However, these publications do not teach the vectored antigen configuration, the FPV insertion sites, or the promoter sequences and arrangement of the present invention.

A foreign gene of interest targeted for insertion into the genome of FPV may be obtained from any pathogenic organism of interest. Typically, the gene of interest will be derived from pathogens that cause diseases in poultry that have an economic impact on the poultry industry. The genes may be derived from organisms for which there are existing vaccines, and because of the novel advantages of the vectoring technology the resulting FPV-derived vaccines will be superior. Also, the genes of interest may be derived from pathogens for which there are currently no vaccines but where there is a requirement for control of a disease. Typically, the gene of interest encodes an immunogenic polypeptide of the pathogen, and may represent surface protein, secreted protein or structural protein.

One relevant avian pathogen that is a target for FPV vectoring in the present invention is Infectious Laryngotracheitis virus (ILT). ILT is a member of the herpesviridiae family, and this pathogen causes an acute disease of chickens which is characterized by respiratory depression, gasping and expectoration of bloody exudate. Viral replication is limited to cells of the respiratory tract, where in the trachea the infection gives rise to tissue erosion and hemorrhage. In chickens, no drug has been effective in reducing the degree of lesion formation or in decreasing clinical signs. Vaccination of birds with various modified forms of the ILT virus derived by cell passage and/or tedious regimes of administration have conferred acceptable protection in susceptible chickens. However because of the degree of attenuation of current ILT vaccines, care must be taken to assure that the correct level of virus is maintained; enough to provide protection, but not enough to cause disease in the flock.

An additional target for the FPV vectoring approach is Newcastle disease, an infectious, highly contagious and debilitating disease that is caused by the Newcastle disease virus (NDV), a single-stranded RNA virus of the paramyxovirus family. The various pathotypes of NDV (velongic, mesogenic, lentogenic) differ with regard to the severity of the disease, as well as the specificity and symptoms, but most types seem to infect the respiratory system and the nervous system. NDV primarily infects chickens, turkeys and other avian species. Historically, vaccination has been used to prevent disease, but because of maternal antibody interference, life-span of the bird and route of administration, the producer needs to adapt immunization protocols to fit specific needs.

Marek's disease of poultry is a lymphoproliferative tumor producing disease of poultry that primarily affects the peripheral nervous system and other visceral tissues and organs. Marek's disease exists in poultry producing countries throughout the world, and is an additional target described by the present invention for a FPV-based vectored vaccine. The causative agent of Marek's disease is a cell associated gammaherpesvirus that has been designated as Marek's disease virus (MDV). Three classes of viruses have been developed as conventional vaccines for protecting chickens against Marek's disease: attenuated serotype 1 MDV, herpesvirus of turkeys (HVT), and naturally avirulent serotype 2 isolates of MDV. Protection obtained with these vaccines is principally directed toward the tumorigenic aspect of the disease. The occurrence of excessive Marek's disease losses in such conventionally vaccinated flocks has led to the requirement for forming admixtures of the various vaccine types. Such polyvalent vaccines while generally ore effective in disease control, complicate the vaccine regime.

SUMMARY OF THE INVENTION

Specifically, the present invention provides a genetically-engineered fowlpox virus designated S-FPV-043 (ATCC Accession No. VR 2395). The present invention also provides a vaccine which comprises an effective immunizing amount of the genetically engineered fowlpox virus designated S-FPV-043 and a suitable carrier. The invention further provides a method of immunizing the animal against disease caused by fowlpox virus and Newcastle disease virus which comprises administering to an animal an effective immunizing dose of the vaccine of the present invention.

Figure 1A:
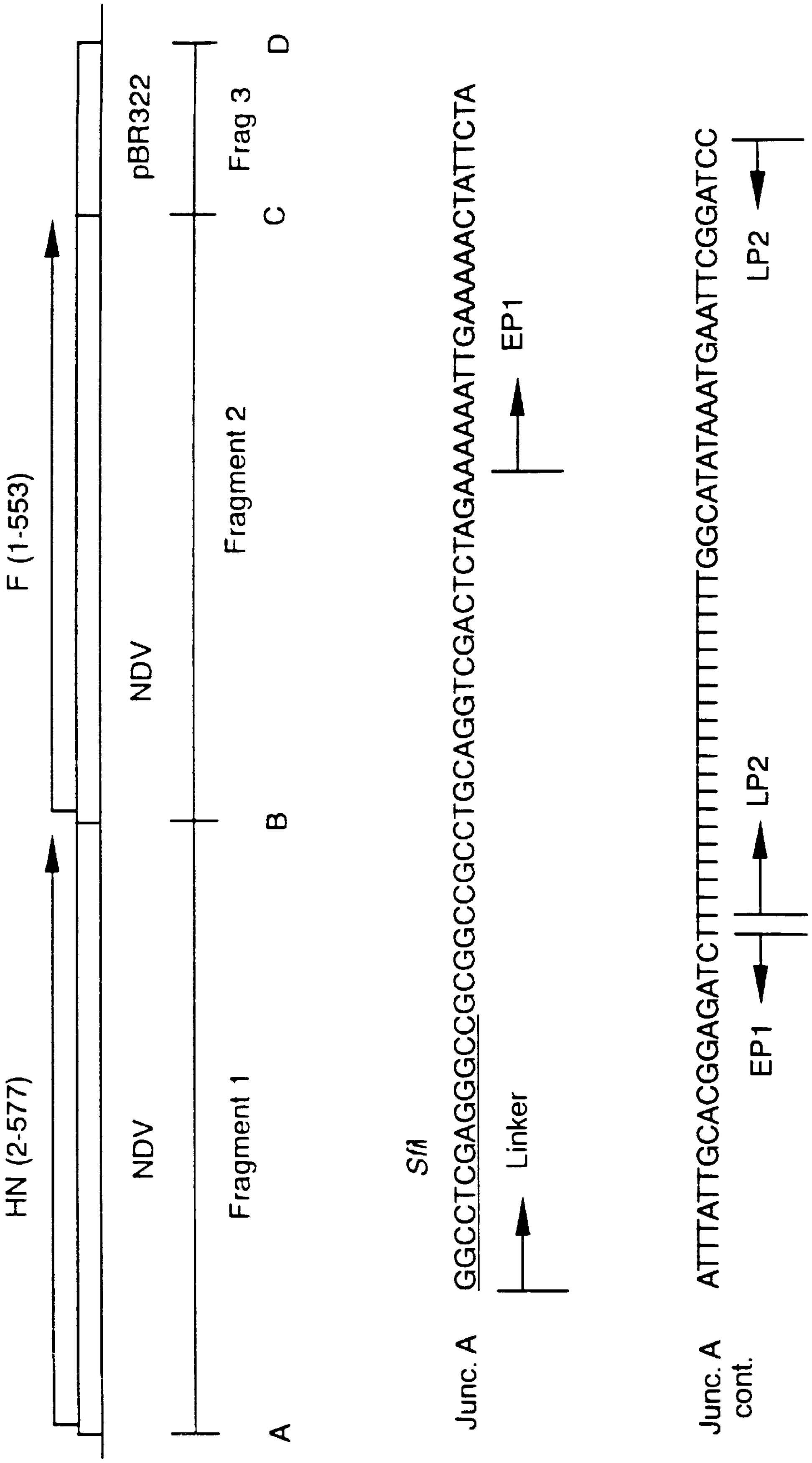
FIG. 1A, FIG. 1B and FIG. 1C

Detailed description of the SfiI fragment insert in Homology Vector 502-26.22. The diagram shows the orientation of DNA fragments assembled in the cassette. The origin of each fragment is described in the Materials and Methods section. The sequences located at the junctions between each fragment and at the ends of the marker gene are shown, including junction A (SEQ ID NO: 15), junction B (SEQ ID NO: 16), junction C (SEQ ID NO: 17), and junction D (SEQ ID NO: 18). The restriction sites used to generate each fragment are indicated at the appropriate junction. The location of the NDV F and HN genes is shown. Numbers in parenthesis ( ) refer to amino acids, and restriction sites in brackets [ ] indicate the remnants of sites which were destroyed during construction.

DETAILED DESCRIPTION OF THE INVENTION

The present invention provides a genetically-engineered fowlpox virus designated S-FPV-043 (ATCC Accession No. VR 2395). The S-FPV-043 has been deposited pursuant to the Budapest Treaty on the International Deposit of Microorganisms for the Purposes of Patent Procedure with the Patent Culture Depository of the American Type Culture Collection, 12301 Parklawn Drive, Rockville, Md. 20852 U.S.A. under ATCC Accession No. VR 2395. The present invention also provides a vaccine which comprises an effective immunizing amount of the attenuated, genetically-engineered fowlpox virus designate S-FPV-043 and a suitable carrier. The vaccine may contain either inactivated or live fowlpox virus S-FPV-043 although live virus is presently preferred.

Suitable carriers for use with the fowlpox virus are well known in the art and include proteins, sugars, etc. One example of such a suitable carrier is a physiologically balanced culture medium containing one or more stabilizing agents such as stabilized, hydrolyzed proteins, lactose, etc.

For purposes of this invention, an "effective immunizing amount" of the S-FPV-043 virus is an amount within the range of $10^2$–$10^9$ PFU/dose. Preferably, the effective immunizing amount is from about $10^3$–$10^5$ PFU/dose for the live virus vaccine. Preferably, the live vaccine is created by taking tissue culture fluids and adding stabilizing agents such as stabilized, hydrolyzed proteins.

The present invention also provides a method of immunizing an animal, particularly a poultry such as a chicken or turkey against disease caused by fowlpox virus and Newcastle disease virus. This method comprises administering to the animal or bird an effective immunizing dose of the vaccine of the present invention. The vaccine may be administered by any of the methods well known to those skilled in the art, for example, by intramuscular, subcutaneous, intraperitoneal, intravenous or intradermal injection. Alternatively, the vaccine may be administered intranasally, orally, or ocularly.

Experimental Details

Methods for constructing, selecting and purifying genetically-engineered fowlpox virus S-FPV-043 are detailed in the Materials and Methods section which follows.

One advantage of recombinant FPV as live vaccines is that they may be engineered to express only a limited number of antigens that are needed to confer protective immunity to the corresponding pathogens. Consequently, host animals vaccinated with the recombinant FPV can be distinguished from those which have been infected with the wild type virus by the absence of antigens that are normally present in the wild type virus.

Materials and Methods

PREPARATION OF FOWLPOX VIRUS STOCK SAMPLES. Fowlpox virus samples were prepared by infecting chicken embryo fibroblast (CEF) cells at a multiplicity of infection of 0.01 PFU/cell in a 1:1 mixture of HAM's F10 medium and Medium 199 (F10/199) containing 2 mM glutamine and antibiotics (referred to as CEF negative medium). Prior to infection, the cell monolayers were washed once with CEF negative medium to remove fetal bovine serum. The FPV contained in the initial inoculum (0.5 ml for 10 cm plate; 10 ml for T175 cm flask) was allowed to absorb onto the cell monolayer for two hours, being redistributed every half hour. After this period, the original inoculum was brought up to an appropriate final volume by the addition of complete CEF medium (CEF negative medium plus 2% fetal bovine serum). The plates were incubated at 37° C. in 5% $CO_2$ until cytopathic effect was complete. The medium and cells were harvested, frozen at −70° C., thawed and dispensed into 1.0 ml vials and refrozen at −70° C. Virus titers typically range between $10^8$ and $10^7$ PFU/ml.

PREPARATION OF FPV DNA. For fowlpox virus DNA isolation, a confluent monolayer of CEF cells in a T175 $cm^2$ flask was infected at a multiplicity of 0.1 and incubated 4–6 days until the cells were showing 100% cytopathic effect. The infected cells were harvested by scraping into the medium and centrifuging at 3000 rpm for 5 minutes in a clinical centrifuge. The medium was decanted, and the cell pellet was gently resuspended in 1.0 ml PBS (per T175) and subjected to two successive freeze-thaws (−70° C. to 37° C.). After the last thaw, the cells (on ice) were sonicated two times for 30 seconds each with 45 seconds cooling time in between. Cellular debris was removed by centrifuging (Sorvall RC-5B Superspeed Centrifuge) at 3000 rpm for 5 minutes in an HB4 rotor at 4° C. FPV virions, present in the supernatant, were pelleted by centrifugation at 15,000 rpm for 20 minutes at 4° C. in a SS34 rotor (Sorvall) and resuspended in 10 mM Tris (pH 7.5). This fraction was then layered onto a 36% sucrose gradient (w/v in 10 mM Tris pH 7.5) and centrifuged (Beckman L8-70M Ultracentrifuge) at 18,000 rpm for 60 minutes in a SW41 rotor at 4° C. The virion pellet was resuspended in 1.0 ml of 10 mM Tris pH 7.5 and sonicated on ice for 30 seconds. This fraction was layered onto a 20% to 50% continuous sucrose gradient and centrifuged at 16,000 rpm for 60 minutes in a SW41 rotor at 4° C. The FPV virion band located about three quarters down the gradient was harvested, diluted with 20% sucrose and pelleted by centrifugation at 18,000 rpm for 60 minutes in a SW41 rotor at 4° C. The resultant pellet was then washed once with 10 mM Tris pH 7.5 to remove traces of sucrose and finally resuspended in 10 mM Tris pH 7.5. FPV DNA was then extracted from the purified virions by lysis (four hours at 60° C.) following the addition of EDTA, SDS, and proteinase K to final concentrations of 20 mM, 0.5% and 0.5 mf/ml, respectively. After digestion, three phenol-chloroform (1:1) extractions were conducted and the sample precipitated by the addition of two volumes of absolute ethanol and incubated at −20° C. for 30 minutes. The sample was then centrifuged in an Eppendorf minifuge for five minutes at full speed. The supernatant was decanted, and the pellet air dried and rehydrated in 0.01 M Tris pH 7.5, 1 mM EDTA at 4° C.

MOLECULAR BIOLOGICAL TECHNIQUES. Techniques for the manipulation of bacteria and DNA, including such procedures as digestion with restriction endonucleases, gel electrophoresis, extraction of DNA from gels, ligation, phosphorylation with kinase, treatment with phosphatase, growth of bacterial cultures, transformation of bacteria with DNA, and other molecular biological methods are described by Maniatis et al (1982) and Sambrook et al (1989). Except as noted, these were used with minor variation.

DNA SEQUENCING. Sequencing was performed using the BRL SEQUENASE® KIT (genetically engineered form of T7 DNA polymerase with no 3' to 5' exonuclease activity as compared to native T7 DNA polymerase) and $^{35}$S-dATP (NEN). Reactions using both the dGTP mixes and the dITP mixes were performed to clarify areas of compression. Alternatively, compressed areas were resolved on formamide gels. Templates were double-stranded plasmid subclones or single stranded M13 subclones, and primers were either made to the vector just outside the insert to be sequenced, or to previously obtained sequence. Sequence obtained was assembled and compared using Dnastar software. Manipulation and comparison of sequences obtained was performed with Superclone and Supersee programs from Coral Software.

STRATEGY FOR THE CONSTRUCTION OF SYNTHETIC POX VIRAL PROMOTERS. For recombinant fowlpox vectors synthetic pox promoters offer several advantages including the ability to control the strength and timing of foreign gene expression. We chose to design four promoter cassettes EP1 (SEQ ID NO:8, LP1 (SEQ ID NO:9), EP2 (SEQ ID NO:10), and LP2 (SEQ ID NO:11) based on promoters that have been defined in the vaccinia virus (Bertholet et al. 1986, Davidson and Moss, 1989a, and Davidson and Moss, 1989b). Each cassette was designed to contain the DNA sequences defined in vaccina flanked by restriction sites which could be used to combine the cassettes in any order or combination. Initiator methionines were also designed into each cassette such that inframe fusions could be made at either EcoRI or BamHi sites. A set of translational stop codons in all three reading frames and an early transcriptional termination signal (Earl, et al., 1990) was also engineered downstream of the inframe fusion site. DNA encoding each cassette was synthesized according to standard techniques and cloned into the appropriate homology vectors.

cDNA CLONING PROCEDURE. cDNA cloning refers to the methods used to convert RNA molecules into DNA molecules following state of the art procedures. Applicants' methods are described in (Gubler and Hoffman, 1983). Bethesda Research Laboratories (Gaithersburg, Md.) have designed a cDNA Cloning Kit that is very similar to the procedures used by applicants, and contains a set of reagents and protocols that may be used to duplicate our results.

For cloning virus mRNA species, a host cell line sensitive to infection by the virus was infected at 5–10 plaque forming units per cell. When cytopathic effect was evident, but before total destruction, the medium was removed and the cells were lysed in 10 mls lysis buffer (4 M guanidine thiocyanate, 0.1% antifoam A, 25 mM sodium citrate pH 7.0, 0.5% N-lauroyl sarcosine, 0.1 M beta-mercaptoethanol). The cell lysate was poured into a sterilized Dounce homogenizer and homogenized on ice 8–10 times until the solution was homogenous. For RNA purification, 8 mls of cell lysate were gently layered over 3.5 mls of CsCl solution (5.7 M CsCl, 25 mM sodium citrate pH 7.0) in a Beckman SW41 centrifuge tube. The samples were centrifuged for 18 hrs at 20° C. at 36000 rpm in a Beckman SW41 rotor. The tubes were put on ice and the supernatants from the tubes were carefully removed by aspiration to leave the RNA pellet undisturbed. The pellet was resuspended in 400 μl glass distilled water, and 2.6 mls of guanidine solution (7.5 M guanidine-HCl, 25 mM sodium citrate pH 7.0, 5 mM dithiothreitol) were added. Then 0.37 volumes of 1 M acetic acid were added, followed by 0.75 volumes of cold ethanol and the sample was put at −20° C. for 18 hrs to precipitate RNA. The precipitate was collected by centrifugation in a Sorvall centrifuge for 10 min at 4° C. at 10000 rpm in an SS34 rotor. The pellet was dissolved in 1.0 ml distilled water, recentrifuged at 13000 rpm, and the supernatant saved. RNA was re-extracted from the pellet 2 more times as above with 0.5 ml distilled water, and the supernatants were pooled. A 0.1 volume of 2 M potassium acetate solution was added to the sample followed by 2 volumes of cold ethanol and the sample was put at −20° C. for 18 hrs. The precipitated RNA was collected by centrifugation in the SS34 rotor at 4° C. for 10 min at 10000 rpm. The pellet was dissolved in 1 ml distilled water and the concentration taken by adsorption at A260/280. The RNA was stored at −70° C.

mRNA containing polyadenylate tails (poly-A) was selected using oligo-dT cellulose (Pharmacia #27 5543-0). Three mg of total RNA was boiled and chilled and applied to a 100 mg oligo-dT cellulose column in binding buffer (0.1 M Tris pH 7.5, 0.5 M LiCl, 5 mM EDTA pH 8.0, 0.1% lithium dodecyl sulfate). The retained poly-A+ RNA was eluted from the column with elution buffer (5 mM Tris pH 7.5, 1 mM EDTA pH 8.0, 0.1% sodium dodecyl sulfate). This mRNA was reapplied to an oligo-dT column in binding buffer and eluted again in elution buffer. The sample was precipitated with 200 mM sodium acetate and 2 volumes cold ethanol at −20° C. for 18 hrs. The RNA was resuspended in 50 μl distilled water.

Ten μg poly-A+ RNA was denatured in 20 mM methyl mercury hydroxide for 6 min at 22° C. β-mercaptoethanol was added to 75 mM and the sample was incubated for 5 min at 22° C. The reaction mixture for first strand CDNA synthesis in 0.25 ml contained 1 μg oligo-dT primer (P-L Bio-chemicals) or 1 μg synthetic primer, 28 units placental ribonuclease inhibitor (Bethesda Research Labs #5518SA), 100 mM Tris pH 8.3, 140 mM KCl, 10 mM MgCl2, 0.8 mM dATP, dCTP, dGTP, and dTTP (Pharmacia), 100 microcuries 32P-labeled dCTP (New England Nuclear #NEG-013H), and 180 units AMV reverse transcriptase (Molecular Genetics Resources #MG 101). The reaction was incubated at 42° C. for 90 min, and then was terminated with 20 mM EDTA pH 8.0. The sample was extracted with an equal volume of phenol/chloroform (1:1) and precipitated with 2 M ammonium acetate and 2 volumes of cold ethanol −20° C. for 3 hrs. After precipitation and centrifugation, the pellet was dissolved in 100 μl distilled water. The sample was loaded onto a 15 ml G-100 SEPHADEX® column, (Pharmacia), gel filtration media; fractionation range for globular proteins: 4,000 to 100,000 daltons, (Pharmacia) in buffer (100 mM Tris pH 7.5, 1 mM EDTA pH 8.0, 100 mM NaCl). The leading edge of the eluted DNA fractions were pooled, and DNA was concentrated by lyophilization until the volume was about 100 μl, then the DNA was precipitated with ammonium acetate plus ethanol as above.

The entire first strand sample was used for second strand reaction which followed the Gubler and Hoffman (1983) method except that 50 μg/ml dNTP's, 5.4 units DNA polymerase I (Boerhinger Mannheim #642-711), and 100 units/ml *E. coli* DNA ligase (New England Biolabs #205) in a total volume of 50 microliters were used. After second strand synthesis, the cDNA was phenol/chloroform extracted and precipitated. The DNA was resuspended in 10 μl distilled water, treated with 1 μg RNase A for 10 min at 22° C., and electrophoresed through a 1% agarose gel (Sigma Type II agarose) in 40 mM Tris-acetate buffer pH 6.85. The gel was strained with ethidium bromide, and DNA in the expected size range was excised from the gel and electroeluted in 8 mM Tris-acetate pH 6.85. Electroeluted DNA was lyophilized to about 100 microliters, and precipitated with ammonium acetate and ethanol as above. The DNA was resuspended in 20 μl water.

Oligo-dC tails were added to the DNA to facilitate cloning. The reaction contained the DNA, 100 mM potassium cacodylate pH 7.2, 0.2 mM dithiothreitol, 2 mM $CaCl_2$, 80 μmoles dCTP, and 25 units terminal deoxynucleotidyl transferase (Molecular Genetic Resources #S1001) in 50 μl. After 30 min at 37° C., the reaction was terminated with 10 mM EDTA, and the sample was phenol/chloroform extracted and precipitated as above.

The dC-tailed DNA sample was annealed to 200 ng plasmid vector pBR322 that contained oligo-dG tails (Bethesda Research Labs #5355 SA/SB) in 200 μl of 0.01 M Tris pH 7.5, 0.1 M NaCl, 1 mM EDTA pH 8.0 at 65° C. for 2 min and then 57° C. for 2 hrs. Fresh competent *E. coli* DH-1 cells were prepared and transformed as described by Hanahan (1983) using half the annealed cDNA sample in twenty 200 μl aliquots of cells. Transformed cells were plated on L-broth agar plates plus 10 μg/ml tetracycline. Colonies were screened for the presence of inserts into the ampicillin gene using AMPSCREEN®, ampicillin-resistance screening disks suitable for screening inactivation of the β-lactamase gene responible for ampicillin resistance in *E. coli*. Ampscreen disks are 85 mm filter paper circles impregnated with benzylpenicillin and bromocresol purple. 600 mg of unbuffered benzylpenicillin is dissolved in 4 ml of 0.1% aqueous solution of bromocresol purple, 0.05 ml 0.1 mol/l sodium hydroxide is added. (Bethesda Research Labs #5537 UA), and the positive colonies were picked for analysis.

HOMOLOGOUS RECOMBINATION PROCEDURE FOR GENERATING RECOMBINANT FPV. This method relies upon the homologous recombination between FPV DNA and the plasmid homology vector DNA which occurs in the tissue culture cells containing both FPV DNA and transfected plasmid homology vector. For homologous recombination to occur, monolayers of CEF cells are infected with S-FPV-001 (A mild fowlpox vaccine strain available as BIO-POX™ from Agri-Bio Corporation, Gainsville, Ga.) at a multiplicity of infection of 0.01 PFU/cell to introduce replicating FPV (i.e. DNA synthesis) into the cells. The plasmid homology vector DNA is then transfected into these cells according to the "Infection-Transfection Procedure".

INFECTION-TRANSFECTION PROCEDURE. CEF cells in 6 cm plates (about 80% confluent) were infected with S-FPV-001 at a multiplicity of infection of 0.01 PFU/cell in CEF negative medium and incubated at 37° C. in a humidified 5% $CO_2$ incubator for five hours. The transfection procedure used is essentially that recommended for LIPOFECTIN® Reagent (BRL), 1:1 (w/w) liposome formulation of cationic lipid N-[1-(2,3-dioleyloxy)propyl]-N,N,N-trimethylammonium chloride (DOTMA) and dioleoyl phosphatidyl ethanolamine (DOPE). Briefly, for each 6 cm plate, 15 micrograms of plasmid DNA were diluted up to 100 microliters with $H_2O$. Separately, 50 micrograms of LIPOFECTIN™ Reagent were diluted to 100 microliters with $H_2O$. The 100 microliters of diluted LIPOFECTIN ™ Reagent were added dropwise to the diluted plasmid DNA contained in a polystyrene, 5 ml, snap cap tube and mixed gently. The mixture was then incubated for 15–20 minutes at room temperature. During this time, the virus inoculum was removed from the 6 cm plates and the cell monolayers washed once with CEF negative medium. Three mls of CEF negative medium were added to the plasmid DNA/lipofectin mixture and the contents pipetted onto the cell monolayer. Following overnight (about 16 hours) incubation at 37° C. in a humidified 5% $CO_2$ incubator, the medium was removed and replaced with 5 ml CEF complete medium. The cells were incubated at 37° C. in 5% $CO_2$ for 3–7 days until cytopathic effect from the virus was 80–100%. Virus was harvested as described above for the preparation of virus stocks. This stock was referred to as a transfection stock and was subsequently screened for recombinant virus by the "Plaque Hybridization Procedure For Purifying Recombinant FPV".

PLAQUE HYBRIDIZATION PROCEDURE FOR PURIFYING RECOMBINANT FPV. CEF cell monolayers were infected with various dilutions of the infection/transfection viral stocks, overlaid with nutrient agarose media (equal volumes of 1.2%–1.4% agarose and 2× M199) and incubated 6–7 days for plaque development to occur. The agarose overlay and plate were marked with the same three asymmetrical dots (India ink) to aid in positioning the Nitrocellulose (NC) membrane (cell monolayer) and agarose overlay. The agarose overlay was transferred to the lid of the 10 cm dish and stored at 4° C. The CEF monolayer was overlaid with a pre-wetted (PBS) NC membrane and pressure applied to transfer the monolayer to the NC membrane. Cells contained on the NC membrane were then lysed by placing the membranes in 1.5 ml of 1.5 M NaCl and 0.5 M NaOH for five minutes. The membranes were placed in 1.5 ml of 3 M sodium acetate (pH 5.2) for five minutes. DNA from the lysed cells was bound to the NC membrane by baking at 80° C. for one hour. After this period the membranes were prehybridized with a solution containing 6×SSC, 3% skim milk, 0.5% SDS, salmon sperm DNA (50 μg/ml) and incubated at 65° C. for one hour. Radio-labeled probe DNA (alpha$^{32}$P-dCTP) was added and incubated at 65° C. overnight (12 hours). After hybridization the NC membranes were washed two times (30 minutes each) with 2×SSC at 65° C., followed by two additional washes at 65° C. with 0.5×SSC. The NC membranes were dried and exposed to X-ray film (Kodak X-OMAT, AR) at −70° C. for 12 hours. Plaques corresponding to positive signals seen on the autoradiogram were picked from the agarose overlay, using a pasteur pipette, and were resuspended into 1 ml of CEF media and stored at −70° C. Typically, 5–6 rounds of plaque purification were required to ensure purity of the recombinant virus.

SCREEN FOR FOREIGN GENE EXPRESSION IN RECOMBINANT FPV USING BLACK PLAQUE ASSAYS. To analyze expression of foreign antigens expressed by recombinant fowlpox viruses, monolayers of CEF cells were infected with recombinant FPV, overlaid with nutrient agarose media and incubated for 6–7 days at 37° C. for plaque development to occur. The agarose overlay was removed from the dish, the cells fixed with 100% methanol for 10 minutes at room temperature and air dried. The primary antibody was diluted to an appropriate concentration with PBS and incubated on the cell monolayer for two hours at room temperature. Unbound antibody was removed from the cells by washing three times with PBS at room temperature. A horseradish peroxidase conjugated secondary antibody was diluted with PBS and incubated on the cell monolayer for two hours at room temperature. Unbound secondary antibody was then removed by washing the cells three times with PBS at room temperature. The cells were incubated 15–30 minutes at room temperature with freshly prepared substrate solution (100 μg/ml 4-chloro-1-naphthol, 0.003% $H_2O_2$ in PBS). Plaques expressing the correct antigen stain black.

SCREEN FOR RECOMBINANT FPV EXPRESSING ENZYMATIC MARKER GENES. When the *E. coli* β-galactosidase (lacZ) or β-glucuronidase (uidA) marker gene was incorporated into a recombinant virus the plaques containing recombinants were visualized by a simple assay. The enzymatic substrate was incorporated (300 μg/ml) into the agarose overlay during the plaque assay. For the lacZ marker gene the substrates BLUOGAL ™ (halogenated indolyl-β-D-galactosidase, Bethesda Research Labs) for blue plaques or CPRG (chlorophenol Red Galactopyranoside, Boehringer mannheim) for red plaques were used. For the uidA marker gene the substrate X-Glucuro Chx (5-bromo-4-chloro-3-indolyl-β-D-glucuronic acid Cyclohexylammonium salt, Biosynth AG) was used. Plaques that expressed active marker enzyme turned either red or blue. The plaques were then picked onto fresh cells and purified by further plaque isolation.

HOMOLOGY VECTOR 451-79.95. The plasmid 451-79.95 was constructed for the purpose of inserting the NDV HN gene into FPV. A lacZ marker gene followed by the NDV HN gene was inserted as a cassette into the homology vector 443-88.14 at the unique SfiI site. The cassette may be constructed utilizing standard recombinant DNA techniques (Maniatis et al., 1982 and Sambrook et al., 1989), by joining restriction fragments from the following sources with the synthetic DNA sequences indicated. The first fragment is the synthetic late promoter LP1 (SEQ ID NO:9). The second fragment contains the coding region of *E. coli* lacZ and is derived from plasmid pJF751 (Ferrari et al., 1985). Note that the promoter and lacZ gene are fused so as to express a hybrid protein consisting of 4 amino acids derived from the synthetic promoter followed by amino acids 10 to 1024 of the lacZ gene. The third fragment is another copy of the synthetic late promoter LP1. the fourth fragment contains the coding region of the NDV HN gene and was derived from the full length HN cDNA clone. Note that the promoter and HN gene are fused so as to express a hybrid protein consisting of 4 amino acids derived from the synthetic promoter followed by amino acids 2 to 577 of the HN gene. Both genes are in the opposite transcriptional orientation relative to the ORF1 gene in the parental homology vector.

HOMOLOGY VECTOR 489-21.1. The plasmid 489-21.1 was constructed for the purpose of inserting the NDV HN gene into FPV. The NDV HN gene was inserted as a cassette into the homology vector 443-88.8 at the unique SfiI site. The cassette may be constructed utilizing standard recombinant DNA techniques (Maniatis et al., 1982 and Sambrook et al., 1989), by joining restriction fragments from the following sources with the synthetic DNA sequences indicated. The first fragment is the synthetic early/late promoter EP1LP2 (SEQ ID NO:8/SEQ ID NO:11). The second fragment contains the coding region of the NDV HN gene and was derived from the full length HN cDNA clone. Note that the promoter and HN gene are fused so as to express a hybrid protein consisting of 4 amino acids derived from the synthetic promoter followed by amino acids 2 to 577 of the HN gene. The HN gene is in the opposite transcriptional orientation relative to the ORF in the parental homology vector.

Figure 1B:
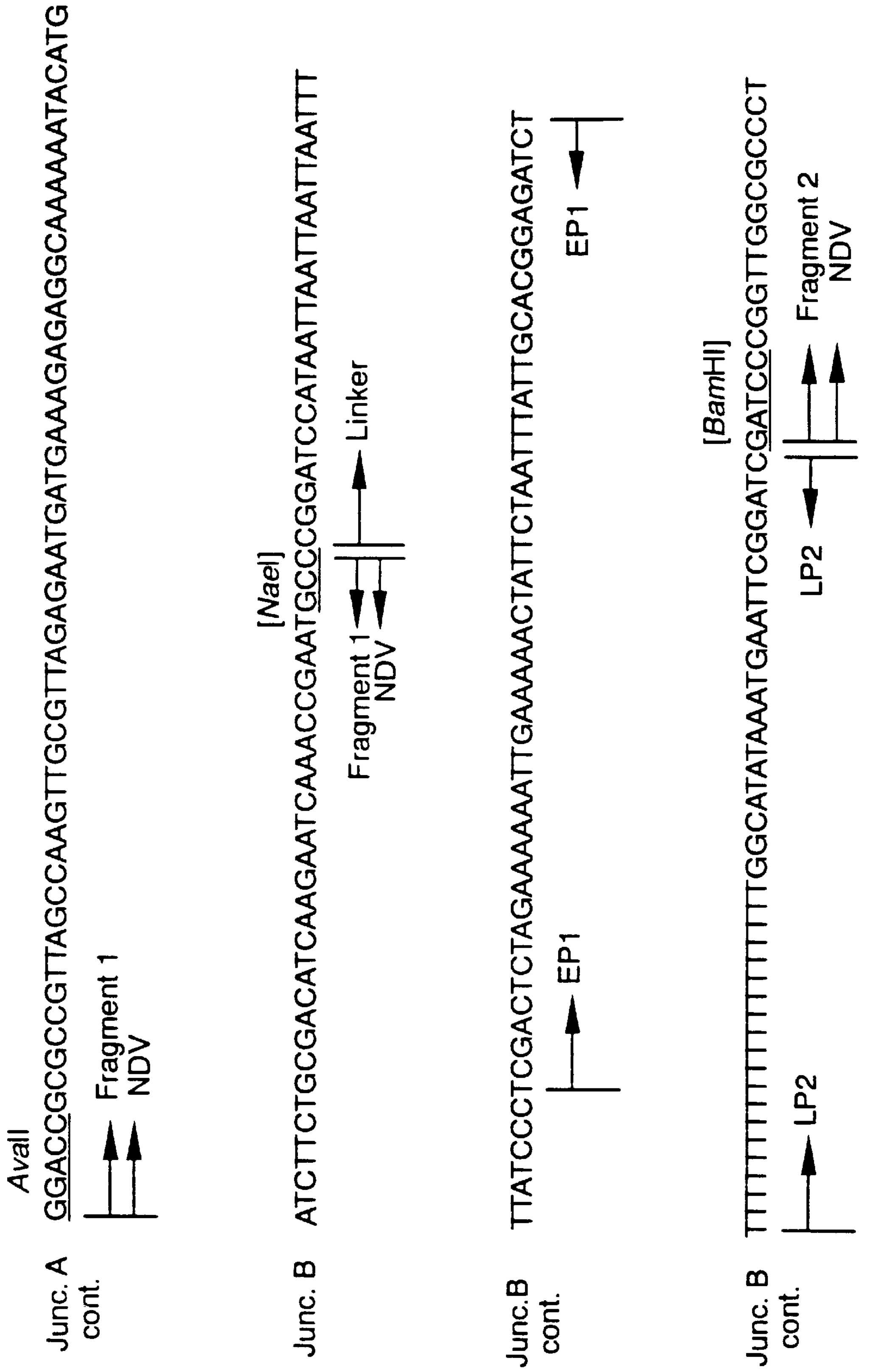
Figure 1C:
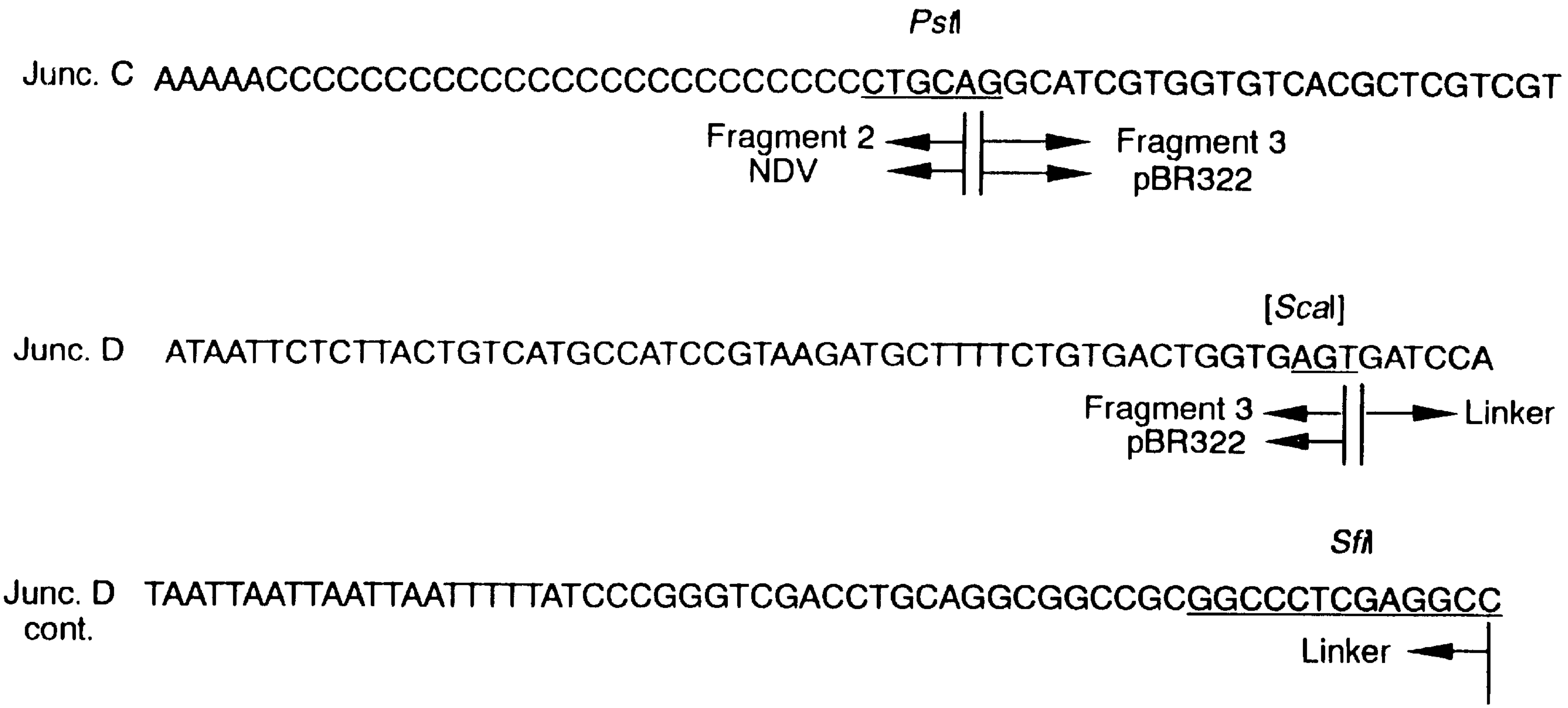

HOMOLOGY VECTORS 502-26.22. The plasmid 502-26.22 was constructed for the purpose of inserting the NDV HN and F genes into FPV. The NDV HN and F genes were inserted as a SfiI fragment (SEQ ID NO:12,13,14) into the homology vector 443-88.8 at the unique SfiI site. The NDV HN and F genes were inserted in the same transcriptional orientation as the ORF in the parental homology vector. A detailed description of the SfiI is shown in FIG. 1. The inserted SfiI fragment may be constructed utilizing standard recombinant DNA techniques (Maniatis et al. and Sambrook et al., 1989), by joining restriction fragments from the following sources with the synthetic DNA sequences indicated in FIG. 1. Fragment 1 is approximately 1811 base pair AvaII to NaeI restriction fragment of the full length NDV HN cDNA clone (B1 strain). Fragment 2 is an approximately 1812 base pair BamHI to PstI restriction fragment of the full length NDV F cDNA (B1 strain). Fragment 3 is an approximately 235 base pair PstI and ScaI restriction fragment of the plasmid pBR322.

HOMOLOGY VECTOR 502-27.5. The plasmid 502-27.5 was constructed for the purpose of inserting the NDV F gene into FPV. A LacZ marker gene followed by the NDV F gene was inserted as a cassette into the homology vector 443-88.14 at the unique SfiI site. The cassette may be constructed utilizing standard recombinant DNA techniques (Maniatis et al., 1982 and Sambrook et al., 1989), joining restriction fragments from the following sources with the synthetic DNA sequences indicated. The first fragment is the synthetic late promoter LP1 (SEQ ID NO:9). The second fragment contains the coding region of *E. coli* LacZ and is derived from plasmid pJF751 (Ferrari et al., 1985). Note that the promoter and LacZ gene are fused so as to express a hybrid protein consisting of 4 amino acids derived from the synthetic promoter followed by amino acids 10 to 1024 of the LacZ gene. The third fragment is the synthetic early/late promoter EP1LP2 (SEQ ID NO:8/SEQ ID NO:11). The fourth fragment contains the coding region of the NDV F gene and was derived from the full length F cDNA clone. Note that the promoter and F gene are fused so as to express a hybrid protein consisting of 4 amino acids dervied from the synthetic promoter followed by 10 amino acids derivied from the F gene 5' untranslated region followed by amino acid 1 to 544 of the F gene. Both genes are in the opposite transcriptional orientation relative to the ORF in the parental homology vector.

HOMOLOGY VECTOR 586-36.6. The plasmid 586-36.6 was constructed for the purpose of inserting the infectious laryngotracheitis virus (ILT) gB and gD genes into the FPV. An *E. coli* β-glucuronidase uidA marker gene preceeded by the ILT gB and gD genes was inserted as a cassette into the homology vector 451-08.22 at the unique SfiI site. The cassette may be constructed utilizing standard recombinant DNA techniques (Maniatis et al., 1982 and Sambrook et al., 1989), by joining restriction fragments from the following sources with the synthetic DNA sequences indicated. The first fragment is the synthetic early/late promoter EP1LP2 (SEQ ID NO:8/SEQ ID NO:11). The second fragment contains the coding region of ILT gB and is dervied from an approximately 3000 base pair ILT virus genomic EcoRI fragment. Note that the promoter and gB gene are fused so as to express the complete coding region of the gB gene (amino acids 1–883). The third fragment is the synthetic early/late promoter EP1LP2 (SEQ ID NO:8/SEQ ID NO:11). The fourth fragment contains the coding region of the ILT gD gene (SEQ ID NO:19,20) and was derived from an approximately 2060 base pair EcoRI to BclI restriction sub-fragment of the ILT KpnI genomic restriction fragment #8 (10.6 KB). Note that the promoter and gD gene are fused so as to express a hybrid protein consisting of 3 amino acids dervied from the synthetic promoter followed by amino acids 3 to 434 of the gD gene. The fifth fragment is the synthetic late promoter LP1 (SEQ ID NO:9). The last fragment contains the coding region of *E. coli* uidA and is derived from plasmid pRAJ260 (Clonetech). Note that the promoter and uidA gene are fused so as to express a hybrid protein consisting of 3 amino acids derived from the synthetic promoter followed by amino acids 1 to 602 of the uidA gene. All three genes are in the opposite transcriptional orientation relative to ORF1 in the parental homology vector.

HOMOLOGY VECTOR 608-10.3. The plasmid 608-10.3 was constructed for the purpose of inserting the Marek's Disease virus (MDV) gD and gB genes into FPV. A LacZ marker gene preceeded by the MDV gD and gB genes was inserted as a cassette into the homology vector 443-88.14 at the unique SfiI site. The cassette may be constructed utilizing standard recombinant DNA techniques (Maniatis et al., 1982 and Sambrook et al., 1989), by joining restriction fragments from the following sources with the synthetic DNA sequences indicated. The first fragment is the synthetic late/early promoter LP2EP2 (SEQ ID NO:11/SEQ ID NO:10). The second fragment contains the coding region of MDV gD and is derived from an approximately 2177 base pair NcoI to SalI sub-fragment of the MDV BglII 4.2 KB genomic restriction fragment (Ross, et al., 1991). Note that the promoter and gD are fused so as to express a hybrid protein consisting of 3 amino acids derived from the synthetic promoter followed by amino acids 3 to 403 of the gD gene. The third fragment is the synthetic early/late promoter EP1LP2 (SEQ ID NO:8/SEQ ID NO:11). The fourth fragment contains the coding region of the MDV gB gene and was derived from an approximately 3898 base pair SalI to EcoRI genomic MDV fragment (Ross, et al., 1989). Note that the promoter and gB gene are fused so as to express a hybrid protein consisting of 3 amino acids derived from the synthetic promoter followed by amino acids 3 to 865 of the gB gene. The fifth fragment is the synthetic late promoter LP1 (SEQ ID NO:9). The sixth fragment contains the coding region of *E. coli* LacZ and is derived from plasmid pJF751 (Ferrari, et al., 1985). Note that the promoter and LacZ gene are fused so as to express a hybrid protein consisting of 4 amino acids dervied from the synthetic promoter followed by amino acids 10 to 1024 of the LacZ gene. All three genes are in the opposite transcriptional orientation relative to ORF1 in te parental homology vector.

EXAMPLES

Example 1

Sites for Insertion of Foreign DNA into FPV

In order to define appropriate insertion sites, a library of FPV EcoRI restriction fragments was generated in the plasmid vector pSP64 (Promega). Several of these restriction fragments were subjected to restriction mapping analysis. Unique blunt cutting restriction endonuclease sites were identified and mapped within the cloned FPV DNA regions. The blunt restriction sites were converted to Not I and Sfi I sites through the use of synthetic DNA linkers (oligo 66.04; 5'-GGCGGCCGCGGCCCTCGAGGCCA-3' SEQ ID NO: 1 and oligo 66.05; 5' TGGCCTCGAGGGCCGCGGCCGCC 3' SEQ ID NO: 2). A β-galactosidase (lacZ) marker gene was inserted in each of the potential sites. A plasmid containing such a foreign DNA insert may be used according to the HOMOLOGOUS RECOMBINATION PROCEDURE FOR GENERATING RECOMBINANT FPV to construct a FPV containing the foreign DNA. For this procedure to be successful it is important that the insertion site be in a region non-essential to the replication of the FPV and that the site be flanked with FPV DNA appropriate for mediating homologous recombination between virus and plasmid DNAs. The plasmids containing the lacZ marker gene were utilized in the HOMOLOGOUS RECOMBINATION PROCEDURE FOR GENERATING RECOMBINANT FPV. The generation of recombinant virus was determined by the SCREEN FOR RECOMBINANT FPV EXPRESSING ENZYMATIC MARKER GENES. Three sites were successfully used to generate a recombinant viruses. In each case the resulting virus was easily purified to 100%, clearly defining an appropriate site for the insertion of foreign DNA. The three homology vectors used to define these sites are described below.

Example 1A

Homolocy Vector 443-88.8

The homology vector 443-88.8 contains a 3.5 KB FPV genomic EcoRI fragment and is useful for the insertion of foreign DNA into FPV. This EcoRI fragment maps to the approximately 5.5 KB overlap of FPV genomic fragments SalI C and PstI F (Coupar et al., 1990). The NotI/SfiI linker described above was inserted into a unique HpaI site in this fragment. This site is designated the 680 insertion site.

The homology vector 443-88.8 was characterized by DNA sequence analysis. Approximately 1495 base pairs of DNA sequence flanking the HpaI site was determined (SEQ ID NO: 3,4). This sequence indicates that the open reading frame of 383 amino acids spans the HpaI insertion site. The HpaI site interrupts this ORF at amino acid 226. This ORF shows no amino acid sequence homology to any known pox virus genes. Example 1B Homology Vector 443-88.14

The homology vector 443-88.14 contains a 2.8 KB FPV genomic EcoRI fragment and is useful for the insertion of foreign DNA into FPV. The NotI/SfiI linker described above was inserted into a unique SnaBI site in this fragment. This site is designated the 681 insertion site.

The homology vector 443-88.14 was characterized by DNA sequence analysis. The entire sequence of the 2.8 KB fragment was determined (SEQ ID NO: 5,6,7). This sequence indicates that the SnaBI site is flanked on one side by a complete ORF of 422 amino acids (ORF1) reading toward the restriction site and on the other side by an incomplete ORF of 387 amino acids (ORF2) also reading toward the restriction site. Both ORF1 and ORF2 share homology with the vaccinia virus M1L gene (ref). The M1L gene shares homology with the vaccinia virus K1L gene which has been shown to be involved in viral host-range functions.

Example 1C

Homology Vector 451-08.22

The homology vector 451-08.22 contains a 4.2 KB FPV genomic EcoRI fragment and is useful for the insertion of foreign DNA into FPV. The NotI/SfiI linker described above was inserted into a unique StuI site in this fragment. A unique MluI site is located approximately 500 base pairs away from the StuI insertion site. This site is designated the 540 insertion site.

Example 2

Bivalent Vaccines Against Newcastle Disease and Fowlpox

Recombinant FPV expressing proteins from NDV make bivalent vaccines protecting against both Marek's Disease and Newcastle disease. We have constructed several recombinant FPV expressing NDV proteins: S-FPV-013 (example 2A), S-FPV-035 (example 2B), S-FPV-041 (example 2C), S-FPV-042 (example 2D), and S-FPV-043 (example 2E).

Example 2A

S-FPV-013

S-FPV-013 is a recombinant fowlpox virus that expresses at least two foreign genes. The gene for *E. coli* β-galactosidase (lacZ gene) and the gene for Newcastle Disease virus hemagglutinin-neuraminidase (HN) protein were inserted into the 681 insertion site. The lacZ gene is under the control of a synthetic late promoter LP1 and the HN gene is under the control of the synthetic late promoter LP2.

S-FPV-013 was derived from S-FPV-001. This was accomplished utilizing the homology vector 451-79.95 (see Materials and Methods) and virus S-FPV-001 in the HOMOLOGOUS RECOMBINATION PROCEDURE FOR GENERATING RECOMBINANT SPV. The transfection stock was screened by the SCREEN FOR RECOMBINANT FPV EXPRESSING ENZYMATIC MARKER GENES. The final result of red plaque purification was the recombinant virus designated S-FPV-013. This virus was assayed for β-galactosidase expression, purity, and insert stability by multiple passages monitored by the blue plaque assay as described in the materials and methods. After the initial three rounds of purification all plaques observed were blue indicating that the virus was pure, stable and expressing the marker gene.

S-FPV-013 was assayed for expression of NDV specific antigens using the BLACK PLAQUE SCREEN FOR FOR- EIGN GENE EXPRESSION IN RECOMBINANT FPV. An NDV HN specific monoclonal antibody (3-1G-5) was shown to react specifically with S-FPV-013 plaques and not with S-FPV-001 negative control plaques. All S-FPV-013 observed plaques reacted with the monoclonal antibody antiserum indicating that the virus was stably expressing the NDV foreign gene.

Example 2B

S-FPV-035

S-FPV-035 is a recombinant fowlpox virus that express a foreign gene. The Newcastle Disease virus HN gene was inserted at the 680 insertion site (see example 1A). The HN gene is under the control of the synthetic early/late promoter EP1LP2.

S-FPV-035 was derived from S-FPV-001. This was accomplished utilizing the homology vector 489-21.1 (see Materials and Methods) and virus S-FPV-001 in the HOMOLOGOUS RECOMBINATION PROCEDURE FOR GENERATING RECOMBINANT SPV. The transfection stock was screened by the PLAQUE HYBRIDIZATION PROCEDURE FOR PURIFYING RECOMBINANT FPV. The final result of plaque hybridization purification was the recombinant virus designated S-SPV-035.

S-FPV-035 was assayed for expression of NDV specific antigens using the BLACK PLAQUE SCREEN FOR FOREIGN GENE EXPRESSION IN RECOMBINANT FPV. An NDV HN specific monoclonal antibody (3-1G-5) was shown to react specifically with S-FPV-035 plaques and not with S-FPV-001 negative control plaques. All S-FPV-035 observed plaques reacted with the monoclonal antibody indicating that the virus was stably expressing the NDV foreign gene.

Example 2C

S-FPV-041

S-FPV-041 is a recombinant fowlpox virus that expresses at least two foreign genes. The gene for *E. coli* β-galactosidase (lacZ gene) and the gene for Newcastle Disease virus fusion (F) protein were inserted into the 681 insertion site. The lacZ gene is under the control of a synthetic late promoter LP1 and the F gene is under the control of the synthetic early/late promoter EP1LP2.

S-FPV-041 was derived from S-FPV-001. This was accomplished utilizing the homology vector 502-27.5 (see Materials and Methods) and virus S-FPV-001 in the HOMOLOGOUS RECOMBINATION PROCEDURE FOR GENERATING RECOMBINANT SPV. The transfection stock was screened by the SCREEN FOR RECOMBINANT FPV EXPRESSING ENZYMATIC MARKER GENES. The final result of red plaque purification was the recombinant virus designated S-FPV-041. This virus was assayed for β-galactosidase expression, purity, and insert stability by multiple passages monitored by the blue plaque assay as described in the materials and methods. After the initial three rounds of purification all plaques observed were blue indicating that the virus was pure, stable and expressing the marker gene.

S-FPV-041 was assayed for expression of NDV specific antigens using the BLACK PLAQUE SCREEN FOR FOREIGN GENE EXPRESSION IN RECOMBINANT FPV. An NDV F specific monoclonal antibody (5-3F-2) was shown to react specifically with S-FPV-041 plaques and not with S-FPV-001 negative control plaques. All S-FPV-041 observed plaques reacted with the monoclonal antibody indicating that the virus was stably expressing the NDV foreign gene.

Example 2D

S-FPV-042

S-FPV-042 is a recombinant fowlpox virus that expresses at least three foreign genes. The gene for *E.coli* β-galactosidase (lacZ gene) and the gene for Newcastle Disease virus fusion (F) protein was inserted into the 681 insertion site. The lacZ gene is under the control of a synthetic late promoter LP1 and the F gene is under the control of the synthetic early/late promoter EP1LP2. The Newcastle Disease virus hemagglutinin (HN) gene were inserted at the 680 insertion site. The HN gene is under the control of the synthetic early/late promoter EP1LP2.

S-FPV-042 was derived from S-FPV-035. This was accomplished utilizing the homology vector 502-27.5 (see Materials and Methods) and virus S-FPV-035 in the HOMOLOGOUS RECOMBINATION PROCEDURE FOR GENERATING RECOMBINANT SPV. The transfection stock was screened by the SCREEN FOR RECOMBINANT FPV EXPRESSING ENZYMATIC MARKER GENES. The final result of red plaque purification was the recombinant virus designated S-FPV-042. This virus was assayed for β-galactosidase expression, purity, and insert stability by multiple passages monitored by the blue plaque assay as described in the materials and methods. After the initial three rounds of purification all plaques observed were blue indicating that the virus was pure, stable and expressing the marker gene.

S-FPV-042 was assayed for expression of NDV specific antigens using the BLACK PLAQUE SCREEN FOR FOREIGN GENE EXPRESSION IN RECOMBINANT FPV. Monoclonal antibodies specific for both HN (3-1G-5) and F (5-3F-2) were shown to react specifically with S-FPV-042 plaques and not with S-FPV-001 negative control plaques. All S-FPV-042 observed plaques reacted with the monoclonal antibodies indicating that the virus was stably expressing the NDV foreign genes.

Example 2E

S-FPV-043

S-FPV-043 is a recombinant fowlpox virus that expresses at least two foreign genes. The genes for Newcastle Disease virus F protein and HN protein were inserted at the 680 insertion site. The F and HN genes are each under the control of a synthetic early/late promoter EP1LP2.

S-FPV-043 was derived from S-FPV-001. This was accomplished utilizing the homology vector 502-26.22 (see Materials and Methods) and virus S-FPV-001 in the HOMOLOGOUS RECOMBINATION PROCEDURE FOR GENERATING RECOMBINANT SPV. The transfection stock was screened by the PLAQUE HYBRIDIZATION PROCEDURE FOR PURIFYING RECOMBINANT FPV. The final result of plaque hybridization purification was the recombinant virus designated S-SPV-043. The S-FPV-043 has been deposited pursuant to the Budapest Treaty on the International Deposit of Microorganisms for the Purposes of Patent Procedure with the Patent Culture Depository of the American Type Culture Collection, 12301 Parklawn Drive, Rockville, Md. 20852 U.S.A. under ATCC Accession No. VR _____.

S-FPV-043 was assayed for expression of NDV specific antigens using the BLACK PLAQUE SCREEN FOR FOREIGN GENE EXPRESSION IN RECOMBINANT FPV. Monoclonal antibodies specific for both HN (3-1G-5) and F (5-3F-2) were shown to react specifically with S-FPV-043 plaques and not with S-FPV-001 negative control plaques. All S-FPV-043 observed plaques reacted with the monoclonal antibodies antiserum indicating that the virus was stably expressing the NDV foreign genes.

TESTING OF RECOMBINANT FPV EXPRESSING NDV ANTIGENS

Groups of one day old SPF chicks (HyVac Inc.) were immunized with recombinant fowlpox viruses S-FPV-035, S-FPV-041, or S-FPV-043. Non vaccinated controls were also included. Three weeks post-vaccination, the birds were challenged intramuscularly with either virulent NDV or virulent FPV (Table 1). The challenged chicks were observed daily for 14 days for clinical signs and death due to NDV. Non vaccinated control birds showed 100% mortality. S-FPV-043 vaccinated birds showed 100% protection against FPV challenge. Birds vaccinated with S-FPV-035 showed 95% protection compared with 85% seen with birds immunized with S-FPV-041. These results suggest that recombinants expressing HN or F alone provide only partial protection. When both NDV proteins are combined into the same virus S-FPV-043, an enhancement of protection against lethal NDV challenge is obtained, resulting in a lower protective dose. The chicks that were challenged with FPV were scored for pox lesions. Non vaccinated control birds showed no protection against FPV lesions. Birds vaccinated with S-FPV-043 were completely protected from FPV lesions.

The duration of immunity conferred by vaccination with S-FPV-043 was examined. A group of SPF chicks was immunized with S-FPV-043 at one day of age and then challenged six weeks post-vaccination with either NDV or FPV. Complete protection was observed against both NDV and FPV challenge in S-FPV-043 vaccinated birds, whereas non vaccinated controls were totally susceptible to both challenge viruses. These results suggest that the duration of immunity afforded by vaccination with S-FPV-043 would span the life of a broiler bird (~6 weeks).

The effect of vaccinating hens in lay with the recombinant S-FPV-043 was evaluated by assessing egg production post-vaccination. One group of 50 hens was vaccinated and a second group of 50 hens, housed under conditions identical to the vaccinated group, served as non vaccinated controls. Daily egg production was monitored for four weeks post-vaccination. No differences were observed in egg production between the two groups of hens, indicating this vaccine will not adversely affect egg production in laying hens.

A study was conducted to determine whether S-FPV-043 could actively immunize chicks in the presence of maternal antibodies to both NDV and FPV. Chicks obtained from NDV and FPV immunized flocks were vaccinated with S-FPV-043 and three weeks after vaccination, they were challenged with either virulent NDV or virulent FPV. Clinical responses were compared with non vaccinated chicks from the same flock and with non-vaccinated chicks from an antibody negative flock (Table 2). Chicks derived from antibody negative flocks showed 100% mortality after NDV challenge. Protection against NDV challenge, in non-vaccinated chicks known to have maternally derived antibody against NDV, ranged from 30 to 60%. Protection levels increased, to a range of 75 to 85%, when the maternal antibody positive chicks were vaccinated with S-FPV-043 suggesting an active immunization. The increase in NDV protection from 30% to 75% (flock 1) and 55% to 85% (flock 2) clearly demonstrate the ability of S-FPV-043 to partially overcome maternal antibody to both NDV and FPV. A decrease in FPV protection (90%) was observed in flock 1, suggesting some inhibition of FPV replication.

Table 1. Immunity conferred by Fowlpox recombinant vaccines vectoring different genes from Newcastle disease virus.

TABLE 1

Immunity conferred by Fowlpox recombinant vaccines vectoring different genes from Newcastle disease virus.

| VIRUS | DOSE[b] | Challenge[a] NDV | Challenge[a] FPV |
|---|---|---|---|
| FPV/NDV-HN (S-FPV-035) | $8 \times 10^5$ | 95 | NT[c] |
| FPV/NDV-F (S-FPV-041) | $2 \times 10^4$ | 85 | NT |
| FPV/NDV-HN+F (S-FPV-043) | $2 \times 10^3$ | 100 | 100 |
| Controls | none | 0 | 0 |

[a]Percent protection following challenge 3 weeks post-vaccination
[b]PFU/0.1 ml dose
[c]Not tested

TABLE 2

Ability of recombinant vaccine FPV/NDV-HN+F (S-FPV-043) to vaccinate chicks with maternal antibody.

| History | | | | Challenge[a] | | | |
|---|---|---|---|---|---|---|---|
| Flock | Hen Antibody[b] | | | NDV | | FPV | |
| Vaccination | NDV-HI[c] | NDV ELISA | FPV-AGP[d] | Vacc. | Con. | Vacc. | Con. |
| 1 NDV + FPV | 1:36 | 1:1738 | Neg | 75 | 30 | 90 | 0 |
| 2 NDV + FPV | 1:64 | 1:2852 | Neg | 85 | 55 | 100 | 0 |
| 3 NDV only | 1:92 | 1:4324 | Neg | 80 | 60 | 95 | 0 |
| 4 None | Neg | Neg | Neg | — | 0 | — | 0 |

[a]Percent protection following challenge 3 weeks post-vaccination.
[b]Every flock antibody.
[c]HI-Hemagglutination Inhibition Assay
[d]AGP-Agar Gel Precipitation Assay

Example 3

S-FPV-082

S-FPV-082 is a recombinant fowlpox virus that expresses at least five foreign genes. The genes for Newcastle Disease virus F protein and HN protein were inserted at the 680 insertion site. The F and HN genes are each under the control of a synthetic early/late promoter EP1LP2. The gene for *E.coli* β-galactosidase (lacZ gene) and the genes for Marek's Disease virus (MDV) gD and gB were inserted into the 681 insertion site. The lacZ gene is under the control of a synthetic late promoter LP1 and the MDV gD and gB genes are under the control of the synthetic early/late promoters LP2EP2 and EP1LP2 respectively.

S-FPV-082 was derived from S-FPV-043. This was accomplished utilizing the homology vector 608-10.3 (see Materials and Methods) and virus S-FPV-043 in the HOMOLOGOUS RECOMBINATION PROCEDURE FOR GENERATING RECOMBINANT SPV. The transfection stock was screened by the SCREEN FOR RECOMBINANT FPV EXPRESSING ENZYMATIC MARKER GENES. The final result of red plaque purification was the recombinant virus designated S-FPV-082. This virus was assayed for β-galactosidase expression, purity, and insert stability by multiple passages monitored by the blue plaque assay as described in the materials and methods. After the initial three rounds of purification all plaques observed were blue indicating that the virus was pure, stable and expressing the marker gene.

S-FPV-082 was assayed for expression of MDV specific antigens using the BLACK PLAQUE SCREEN FOR FOREIGN GENE EXPRESSION IN RECOMBINANT FPV. Convalescent sera from MDV infected chickens was shown to react specifically with S-FPV-082 plaques and not with S-FPV-001 negative control plaques. All S-FPV-082 observed plaques reacted with the chicken antiserum indicating that the virus was stably expressing the MDV foreign genes.

S-FPV-082 expresses foreign antigens from NDV and MDV. This virus will be valuable as a multi-valent vaccine against Newcastle Disease, Marek's Disease and Fowlpox.

Example 4

S-FPV-083

S-FPV-083 is a recombinant fowlpox virus that expresses at least five foreign genes. The genes for Newcastle Disease virus F protein and HN protein were inserted at the 680 insertion site. The F and HN genes are each under the control of a synthetic early/late promoter EP1LP2. The gene for *E. coli* β-glucuronidase (uidA gene) and the genes for Infectious Laryngotracheitis virus (ILT) gD and gB were inserted into the 540 insertion site. The uidA gene is under the control of a synthetic late promoter LP1 and the ILT gD and gB genes are each under the control of a synthetic early/late promoter (EP1LP2).

S-FPV-083 was derived from S-FPV-043. This was accomplished utilizing the homology vector 586-36.6 (see Materials and Methods) and virus S-FPV-043 in the HOMOLOGOUS RECOMBINATION PROCEDURE FOR GENERATING RECOMBINANT SPV. The transfection stock was screened by the SCREEN FOR RECOMBINANT FPV EXPRESSING ENZYMATIC MARKER GENES. The final result of blue plaque purification was the recombinant virus designated S-FPV-083. This virus was assayed for β-glucuronidase expression, purity, and insert stability by multiple passages monitored by the blue plaque assay as described in the materials and methods. After the initial three rounds of purification all plaques observed were blue indicating that the virus was pure, stable and expressing the marker gene.

S-FPV-083 was assayed for expression of ILT specific antigens using the BLACK PLAQUE SCREEN FOR FOREIGN GENE EXPRESSION IN RECOMBINANT FPV. Convalescent sera from ILT infected chickens was shown to react specifically with S-FPV-083 plaques and not with S-FPV-001 negative control plaques. All S-FPV-083 observed plaques reacted with the chicken antiserum indicating that the virus was stably expressing the ILT foreign genes.

S-FPV-083 expresses foreign antigens from NDV and ILT. This virus will be valuable as a multi-valent vaccine against Newcastle Disease, Infectious Laryngotracheitis and Fowlpox.

References

1. C. Bertholet, et al., *EMBO Journal* 5, 1951–1957, 1986.
2. B. H. Coupar, et al., *Virology* 179, 159–167, 1990.
3. A. J. Davidson and B. Moss, *J. Mol. Biol.* 210, 749–769.
4. A. J. Davidson and B. Moss, *J. Mol. Biol.*, 210, 771–784.
5. P. L. Earl, et al., *Journal of Virology* 64, 2448–2451, 1990.
6. J. Esposito, et al., *Virology* 165, 313.
7. F. A. Ferrari, et al., *Journal of Bacteriology* 161, 556–562, 1985.
8. U. Gubler and B. J. Hoffman, *Gene* 25, 263–269.
9. D. Hanahan, *Molecular Biology* 166, 557–580, 1983.
10. M. A. Innis, et al., *PCR Protocols A Guide to Methods and Applications*, 84–91, Academic Press, Inc., San Diego 1990.
11. Maniatis, et al., *Molecular Cloning*, Cold Spring Harbor Laboratory, New York 1982.
12. L. J. N. Ross, et al., *Journal of General Virology*, 70, 1789–1804 (1989).
13. L. J. N. Ross, et al., *Journal of General Virology*, 72, 949–954 (1991).
14. J. Sambrook, et al., *Molecular Cloning A Laboratory Manual Second Edition*, Cold Spring Harbor Press, 1989.
15. J. Taylor, et al., *Vaccine* 9, 190–193, 1991.

---

What is claimed is:

1. A recombinant fowlpox virus designated S-FPV-043, ATCC Accession No. VR 2395.

2. A vaccine which comprises an effective immunizing amount of the virus of claim 1 and a suitable carrier.

3. The vaccine of claim 2, wherein in the carrier is a physiologically balanced culture medium containing stabilizing agents.

4. The vaccine of claim 2, wherein the effective immunizing amount is $10^3$ to about $10^9$ PFU/dose.

5. The vaccine of claim 2, wherein the effective immunizing amount is about $10^3$ to about $10^5$ PFU/dose.

6. A method of immunizing an animal against fowlpox virus and Newcastle disease virus which comprises administering to the animal an effective immunizing dose of vaccine of claim 2.

7. The method of claim 6, wherein the animal is poultry.

8. The method of claim 6, wherein the animal is a chicken.

9. The method of claim 6, wherein the vaccine is administered by intramuscular, subcutaneous, intraperitoneal, intravenous or intradermal injection.

10. The method of claim 6, wherein the vaccine is administered intranasaly.

11. The method of claim 6, wherein the vaccine is administered orally.

12. The method of claim 6, wherein the vaccine is administered ocularly.

* * * * *